(12) United States Patent
Rotello et al.

(10) Patent No.: US 8,021,891 B2
(45) Date of Patent: *Sep. 20, 2011

(54) METHODS AND COMPOSITIONS FOR PROTEIN DETECTION USING NANOPARTICLE-FLUORESCENT POLYMER COMPLEXES

(75) Inventors: Vincent Rotello, Amherst, MA (US);
Uwe Bunz, Atlanta, GA (US);
Chang-Cheng You, Amherst, MA (US);
Oscar Miranda, Amherst, MA (US);
Ik-Bum Kim, Dublin, OH (US)

(73) Assignee: University of Massachusetts, Boston, MA (US)

( * ) Notice: Subject to any disclaimer, the term of this patent is extended or adjusted under 35 U.S.C. 154(b) by 202 days.

This patent is subject to a terminal disclaimer.

(21) Appl. No.: 12/313,116

(22) Filed: Nov. 17, 2008

(65) Prior Publication Data
US 2009/0221099 A1  Sep. 3, 2009

Related U.S. Application Data

(60) Provisional application No. 61/004,472, filed on Nov. 28, 2007.

(51) Int. Cl.
*G01N 21/76* (2006.01)
(52) U.S. Cl. ........ 436/172; 436/164; 436/169; 436/171; 436/501
(58) Field of Classification Search .................. None
See application file for complete search history.

(56) References Cited

U.S. PATENT DOCUMENTS

2002/0160363 A1* 10/2002 McDevitt et al. ............... 435/6
2010/0021960 A1   1/2010 Rotello et al.

OTHER PUBLICATIONS

Wallace et al., "Indicator Displacement Assay (IDA)," Encyclopedia of Supramolecular Chemistry, 1:1, pp. 1-11, Published on: Mar. 27, 2006.*
Fan et al., "Beyond superquenching: Hyper-efficient energy transfer from conjugated polymers to gold nanoparticles," Proc. Natl. Acad. Sci. U.S.A., 2003, vol. 100, issue 11, pp. 6297-6301.*
Verma et al., "Surface recognition of biomacromolecules using nanoparticle receptors," Chem. Commun., 2005, issue 3, pp. 303-312.*
Haskins-Glusac et al., "Luminescence Quenching of a Phosphorescent Conjugated Polyelectrolyte," J. Am. Chem. Soc., 2004, vol. 126, No. 45, pp. 14964-14971.*
"Handbook of Fluorescent Probes and Research Chemicals", R. P. Haugland, ed., Sixth Edition, 1996, p. 134.*
You, C-C; Miranda, OR; Gider, B; Ghosh, PS; Kim, I-B; Erdogan, B; Krovi, SA; Bunz, UHF; Rotello, VM. Detection and identification of proteins using nanoparticle—fluorescent polymer 'chemical nose' sensors. Nature Nanotechnology vol. 2, pp. 318-323 (May 2007); Published online: Apr. 22, 2007; doi:10.1038/nnano.2007.99.
Miranda, OR; You, C-C; Phillips, R; Kim, I-B; Ghosh, PS; Bunz, UHF; Rotello, VM. Array-Based Sensing of Proteins Using Conjugated Polymers. J. Am. Chem. Soc. 2007, 129, pp. 9856-9857.
Kim, I-B; Dunkhorst, A; Gilbert, J; Bunz, UHF. Sensing of Lead Ions by a Carboxylate-Substituted PPE: Multivalency Effects. Macromolecules 2005, vol. 38, No. 11, pp. 4560-4562. Published on Web May 3, 2005.

* cited by examiner

*Primary Examiner* — Shafiqul Haq
*Assistant Examiner* — Galina Yakovleva
(74) *Attorney, Agent, or Firm* — Milstein Zhang & Wu LLC

(57) ABSTRACT

Compositions, methods and related apparatus, as can be used for selective protein detection and identification.

21 Claims, 15 Drawing Sheets

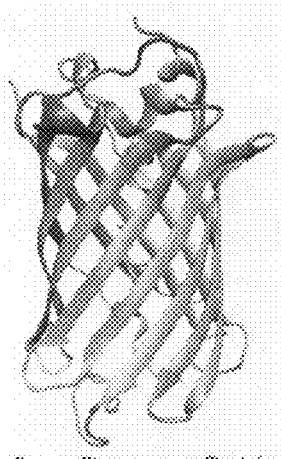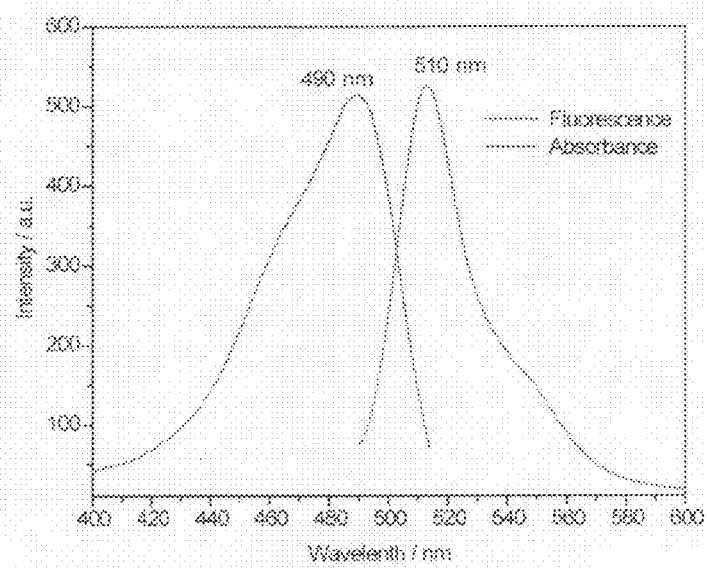
Figure 6A
Figure 6B

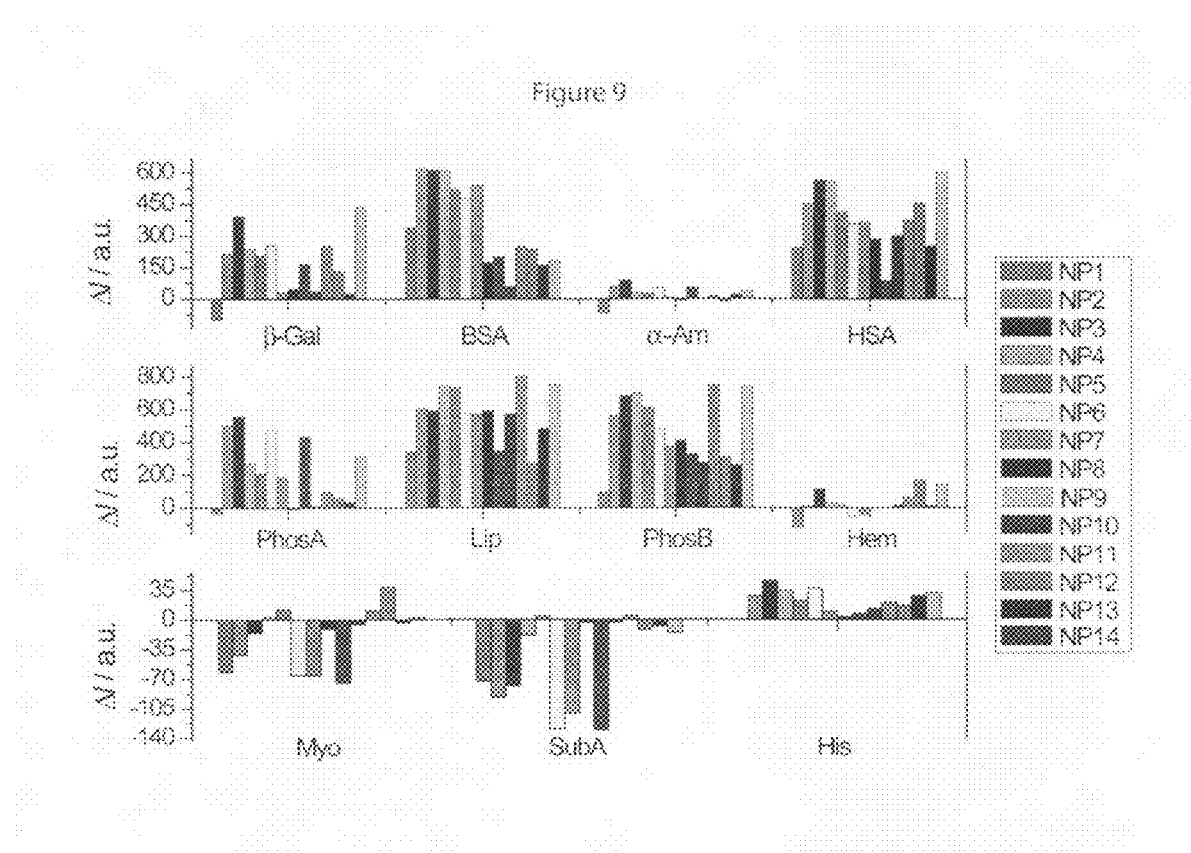

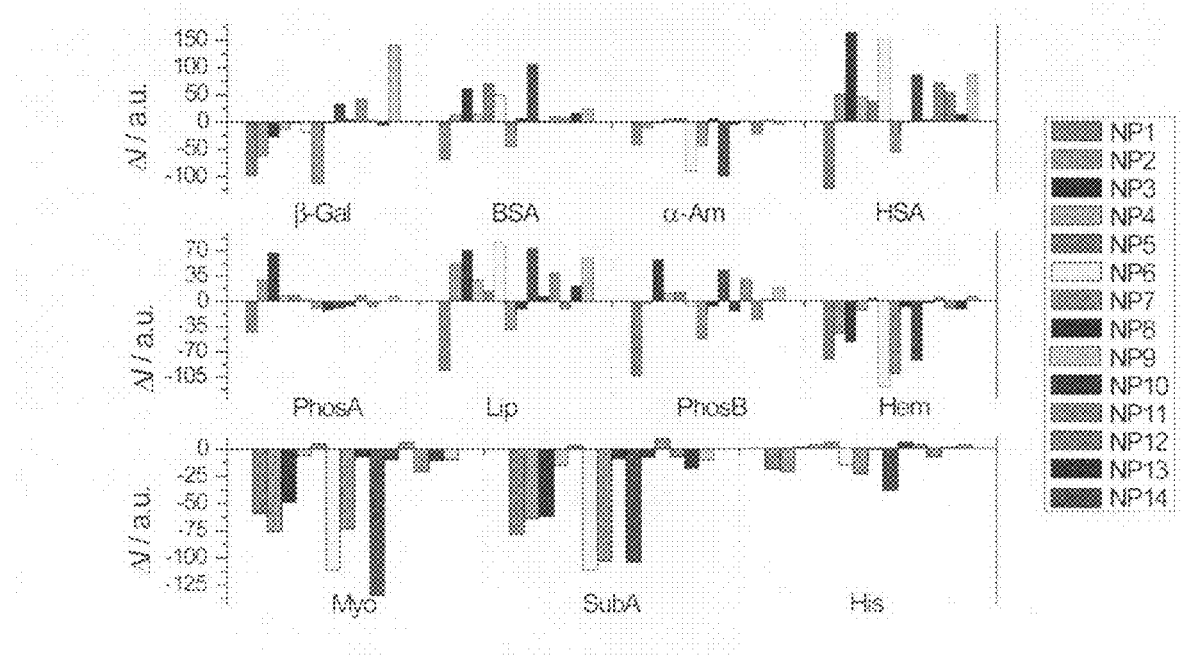

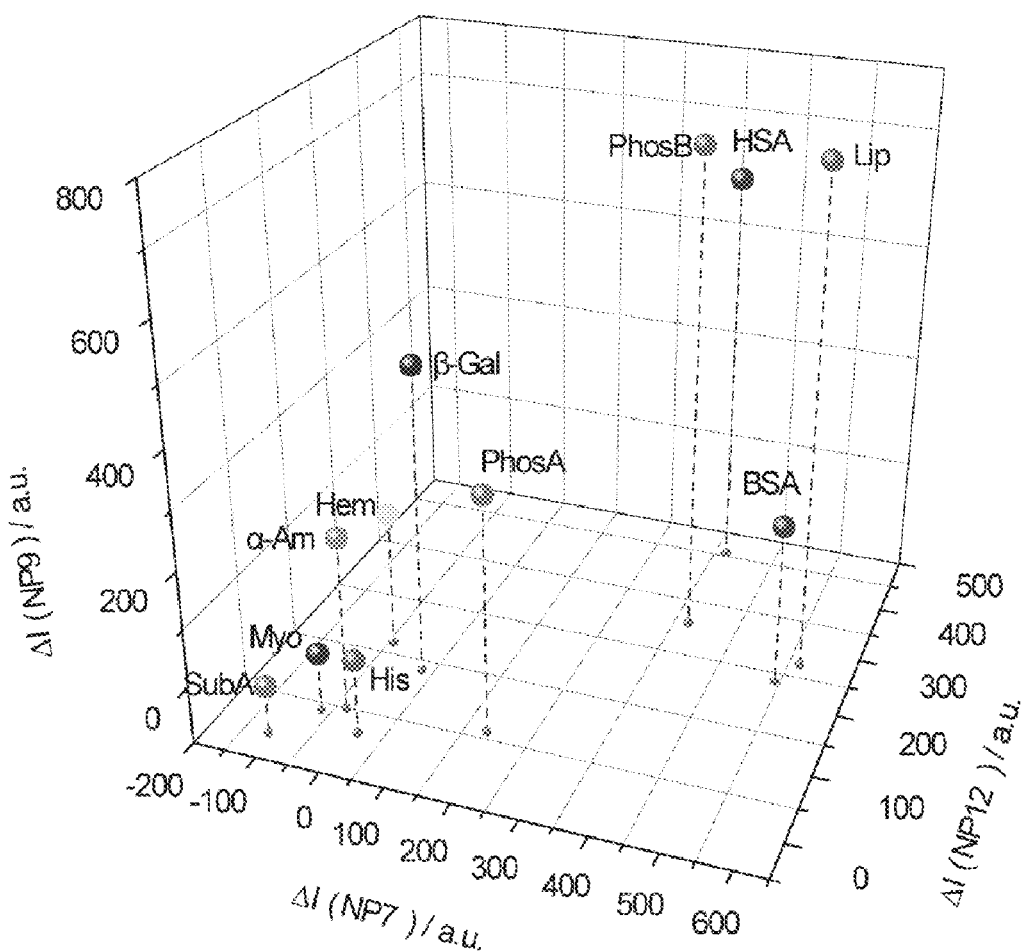

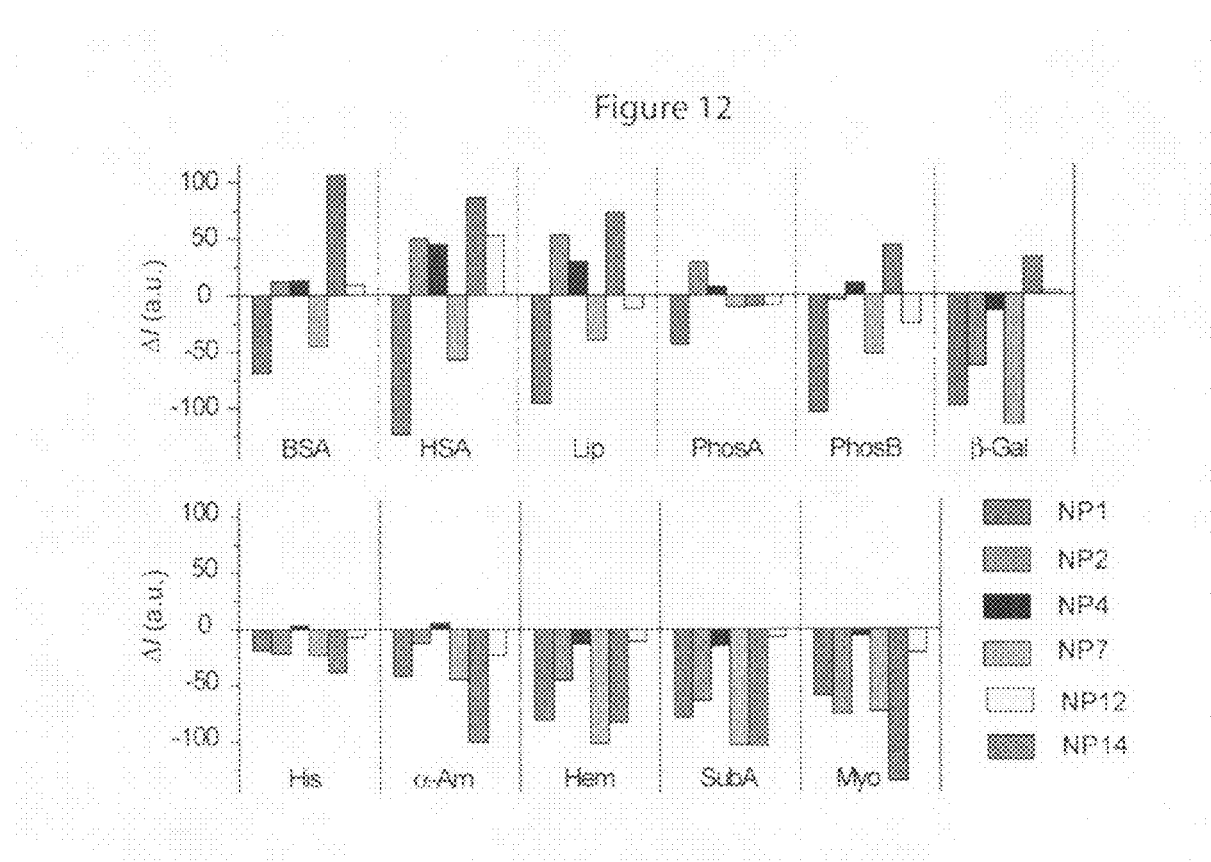

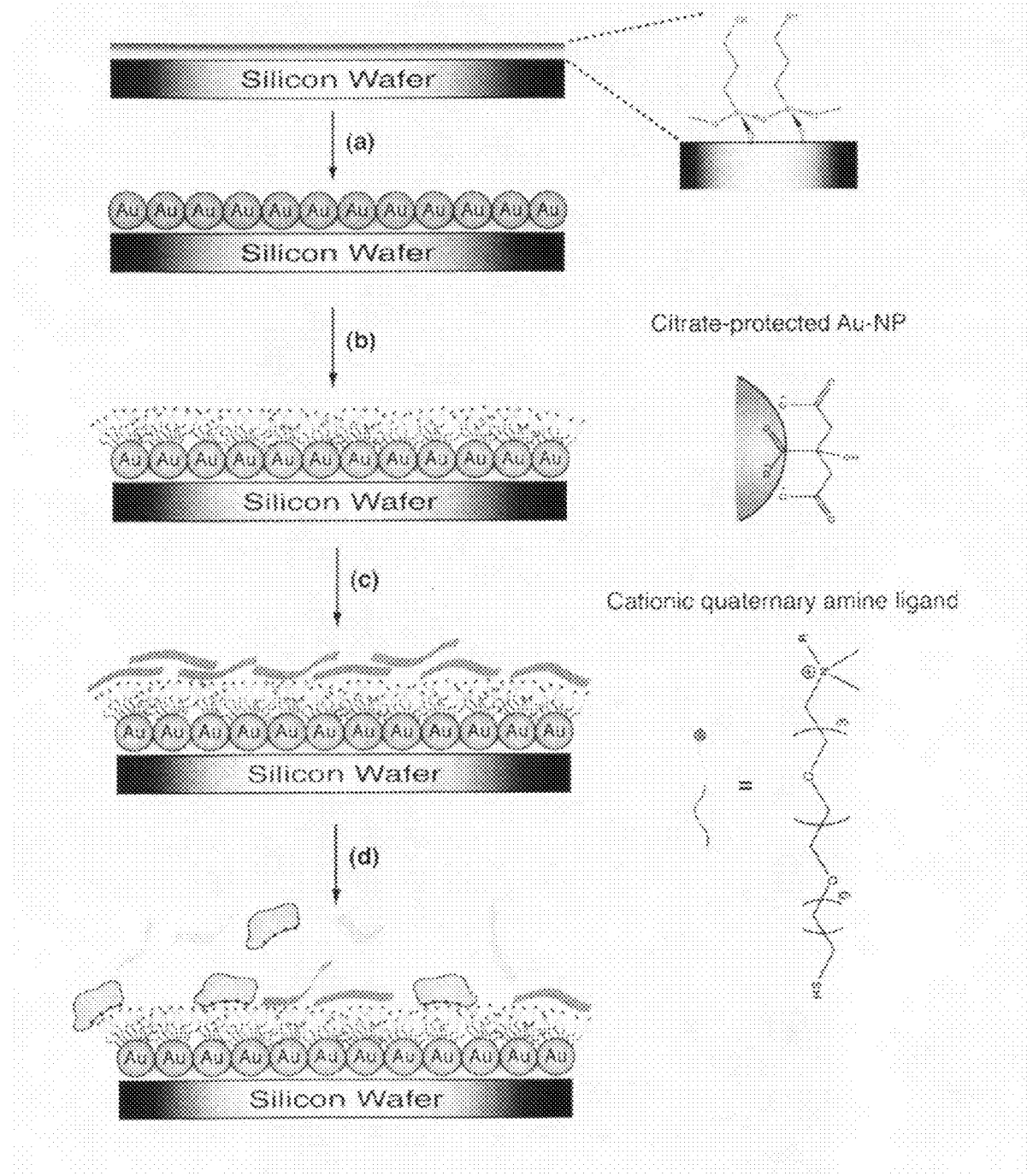

US 8,021,891 B2

METHODS AND COMPOSITIONS FOR PROTEIN DETECTION USING NANOPARTICLE-FLUORESCENT POLYMER COMPLEXES

This application claims priority benefit from application Ser. No. 61/004,472 filed Nov. 28, 2007, the entirety of which is incorporated herein by reference.

The United States Government has certain rights to this invention pursuant to Grant Nos. GM077173 and DMI-0531171 from the National Institutes of Health and the National Science Foundation, respectively, to the University of Massachusetts, and Grant No. DE-FG02-04ER46141 from the Department of Energy to the Georgia Institute of Technology.

BACKGROUND OF THE INVENTION

The presence of certain biomarker proteins and/or irregular protein concentrations is a sign of cancer and other disease states. Sensitive, convenient and precise protein-sensing methods provide crucial tools for the early diagnosis of diseases and successful treatment of patients. However, protein detection is a challenging problem owing to the structural diversity and complexity of the target analytes. At present, the most extensively used detection method for proteins is the enzyme-linked immunosorbent assay (ELISA). In this system, the capture antibodies immobilized onto surfaces bind the antigen through a "lock-key" approach, and another enzyme-coupled antibody is combined to react with chromogenic or fluorogenic substrates to generate detectable signals. Despite its high sensitivity; the application of this method is restricted because of its high production cost, instability and challenges regarding quantification. Although synthetic systems would alleviate some of these concerns, obtaining high affinity and specificity remains quite challenging. As a result, the search for sensitive, efficient and cost-effective protein detection and identification remains an ongoing concern in the art.

SUMMARY OF THE INVENTION

In light of the foregoing, it is an object of the present invention to provide one or more protein detection/identification methods and/or apparatus used therewith, thereby overcoming various deficiencies and shortcomings of the prior art, including those outlined above. It will be understood by those skilled in the art that one or more aspects of this invention can meet certain objectives, while one or more aspects can meet certain other objectives. Each objective may not apply equally, in all its respects, to every aspect of this invention. As such, the following objects can be viewed in the alternative with respect to any one aspect of this invention.

It can be an object of the present invention to provide, in comparison with sensor systems of the prior art, an approach to protein detection and/or identification which is relatively inexpensive, easily prepared and with data quickly processed and analyzed.

It can be another object of the present invention to provide one or more methods for protein detection, to quickly distinguish between proteins over a range of molecular weights, concentrations and surface structural features without resort to marker systems of the prior art.

It can be another object of the present invention, alone or in conjunction with one or more of the preceding objectives, to provide an apparatus and/or kit for ready use in the detection and/or identification of protein analytes and/or biomarkers.

Other objects, features, benefits and advantages of the present invention will be apparent from this summary and the following descriptions of certain embodiments, and will be readily apparent to those skilled in the art having knowledge of various fluorescence-based detection methods. Such objects, features, benefits and advantages will be apparent from the above as taken into conjunction with the accompanying examples, data, figures and all reasonable inferences to be drawn therefrom.

In part, the present invention can be directed to a method of detecting the presence of a protein analyte. Such a method can comprise providing a non-covalent sensor complex comprising a metal, metallic, semiconductor or other particle component (e.g., cationic) and a polymer fluorophore or other quencher component (e.g., anionic) chemically complementary to the particle component, such a complex having an initial background or reference fluorescence; irradiating such a sensor complex; and monitoring an effect and/or change in fluorescence, such monitoring as can indicate no change, no analyte presence and/or a change not associated with an analyte of interest, and any such change as can be indicative of the presence of at least one protein analyte. In certain embodiments, such a particle component can be nanodimensioned and can comprise a hydrophilic moiety. In certain other embodiments, such a component can comprise a hydrophobic moiety. Regardless, ionic (e.g., cationic) character can be provided with a quaternary ammonium or other charged group. The compositional identity and/or dimension of such a particle component is limited only by protein surface interaction. Likewise, the composition of any such fluorophore component is limited only by complementary chemistry (e.g., anionic) with a particle component, measurable fluorescence and/or change thereof responsive to protein contact or interaction.

Regardless, in certain other embodiments, such a method can comprise a plurality of sensor complexes, each such complex as can provide a change in fluorescence responsive to the presence of at least one protein. As illustrated below, such complexes can be varied by fluorophore, particle and/or linker component, such variations as would be known to those skilled in the art made aware of this invention. Protein interaction can provide a fluorescence pattern indicative of the presence of a particular protein analyte.

In part, the present invention can also be directed to a method of using fluorescent polymer, biopolymer or fluorogenic biopolymer displacement to detect and/or identify protein(s). Such a method can comprise providing a sensor complex of the sort described above, irradiated for a time and/or at a wavelength at least partially sufficient for initial fluorescence (e.g., background fluorescence as can be due to quenching by a particle component); contacting such a complex with a protein analyte, such contact and/or protein in an amount at least partially sufficient to affect fluorescence (e.g., the intensity or wavelength thereof); and monitoring the change in fluorescence upon such contact. The sensor complex employed with such a method can comprise one of those discussed above or illustrated elsewhere herein, alone or in combination with one or more other complexes as can be present. Regardless, such a complex can be irradiated at a wavelength at least partially sufficient for electronic excitement and/or fluorescence thereof. Likewise, as discussed above and illustrated elsewhere herein, contact with such a protein can be for a time and/or at a concentration at least partially sufficient to interact with the metallic (e.g., without limitation metal, precious metal, metal oxide, sulfide or selenide and/or semiconductor) nanoparticle component of such a complex and/or to affect fluorescence of the fluorophore component. Alternatively, a protein can interact with a polymer component, displacing the particle and altering the fluorescence of the complex. Such a protein can be present in the context of an unknown sample or mixture, the identity of which is limited by competitive and/or preferential interaction with such a particle or polymer component, as compared to particle component-fluorophore interaction. In certain embodiments, the presence of such a protein and preferential interaction can be observed to enhance fluorescent excited state, as can be indicated by a change in wavelength or intensity of fluorescence.

In part, the present invention can also be directed to a method detecting the presence of and/or identifying one or more unknown proteins. Such a method can comprise providing reference spectral data comprising change in fluorescence for interaction of a sensor complex, of the sort described above, with a plurality of reference proteins or reference protein-containing samples; comparing such reference data with change in fluorescence for interaction of such a sensor complex with unknown protein(s); and identifying the protein(s) on the basis of such a comparison. In certain embodiments, such reference data can comprise fluorescence changes from interaction of a plurality of such complexes with reference protein(s) or reference protein-containing samples. As described above, such complexes can be varied by fluorophore component (e.g., π-conjugation and substitution) and/or fluorescence thereof. Without limitation as to number of sensor complexes employed comprising the reference data, protein identification can be made by direct spectral comparison. Use of a plurality of sensor complexes can provide a pattern of fluorescence changes, each such pattern as can be indicative of the presence of a particular protein analyte or a particular protein expression signature. Alternatively, comparison can be made using one or more discriminate analysis techniques, as described below.

Alone or in conjunction with discriminate analysis, the present invention can also be directed to an apparatus for detection and/or identification of protein analytes and/or biomarkers. Without limitation as to physical embodiment or configuration, such a sensor apparatus can comprise a matrix comprising an array of a plurality of sensor complexes of the sort described herein. As illustrated below, such complexes can be chosen to provide differential changes in fluorescence, each such change responsive to a wide range of proteins. Fluorescence change upon protein interaction and comparison with reference spectral data, as described above, can be used for discriminate protein identification.

Likewise, alone or in conjunction with one or more of the methodologies described herein, the present invention can also be directed to a kit for detection and/or identification of a protein in an analyte sample. Such a kit can comprise one or more nanoparticle components and one or more fluorophore components, each as described above or as would otherwise be understood by those skilled in the art made aware of this invention, for non-covalent bonding of one to another. Such a kit can optionally comprise a fluid medium conducive for protein interaction and/or fluorescence. Regardless, such a kit can also comprise a solid matrix component as can be employed with a plurality of such non-covalent sensor complexes and/or protein analytes, biomarkers, samples and/or mixtures thereof.

Without limitation as to methodology, apparatus, kit or application context, the present invention can be directed to a nano-dimensioned particulate comprising a core component and a coating component on or coupled thereto, such a coating component as can comprise charged or otherwise interactive terminal groups. In certain embodiments, such a core component can, without limitation, comprise a metal, a metal oxide and/or a semiconductor material. Notwithstanding core identity, such a coating component can comprise ligands bearing a hydrophilic moiety or a hydrophobic moiety, the latter as can be selected from alkyl, oxa-substituted alkyl and/or poly(alkylene oxide) moieties. Regardless, such moieties can bridge such a terminal group, including but not limited to quaternary ammonium, and a coupling group including but not limited to sulfide. The coating component can also comprise polyelectrolytes including but not limited to polylysine, polyallylamine, polyethyleneimine, and their crosslinked entities. Such coatings and/or core components can be selected from those described more fully herein or as would be understood by those skilled in the art made aware of this invention, such selections and/or combinations limited only by protein interaction of the sort described herein.

Likewise, without limitation as to methodology, apparatus, kit or conjugation with one or more of the aforementioned particulates, this invention can be directed to a fluorogenic polymer of a formula

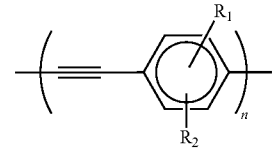

wherein $R_1$ and $R_2$ can be moieties independently selected from H and interactive moieties including but not limited to charged moiety and counter ion pairs, such a selection at least partially sufficient for non-covalent interaction of such a polymer component with a particulate of the sort discussed above; and n can be an integer greater than 1 and corresponding to a number of repeating units as can be selected for desired π-conjugation, polymer fluorescence and/or quantum yield, such a component as can be terminated as described herein or as would be understood by those skilled in the art, depending upon reagent and/or reaction conditions. Without limitation, in certain embodiments, $R_1$ and $R_2$ independently comprise carboxylate and/or sulfate groups and corresponding alkali metal counter ions.

Alternatively, without limitation as to methodology, apparatus, kit or conjugation with one or more of the aforementioned particulates, this invention can be directed to a fluorogenic polymer of a formula

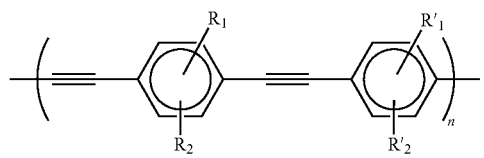

wherein $R_1$ and $R_2$ can be moieties independently selected from H, alkyl, oxa-substituted alkyl moieties and/or a moiety sterically configured to at least partially suppress non-specific polymer-pathogen interactions, providing at least one of $R_1$ and $R_2$ as such a steric configuration; and $R'_1$ and $R'_2$ can be moieties independently selected from charged moiety and counter ion pairs, such a selection at least partially sufficient for non-covalent interaction of such a polymer component with a particulate of the sort discussed above; and n can be an integer greater than 1 and corresponding to a number of repeating units as can be selected for desired π-conjugation, polymer fluorescence and/or quantum yield, such a component as can be terminated as described herein or as would be understood by those skilled in the art, depending upon reagent and/or reaction conditions. In certain non-limiting embodiments, $R_1$ and $R_2$ can be independently selected from linear and branched oxa-substituted alkyl (e.g., poly(alkylene oxide)) moieties and $R'_1$ and $R'_2$ can independently comprise carboxylate and/or sulfate groups and corresponding alkali metal counter ions. Without limitation, various such fluorogenic polymers are described in a co-pending application, entitled "Methods and Compositions for Pathogen Detection Using Fluorescent Polymer Sensors," filed contemporaneously herewith, the entirety of which is incorporated herein by reference.

As illustrated elsewhere herein, other fluorogenic polymers and/or bipolymers can be used in conjunction with various particle components, apparatus and/or methods of this invention, such a polymer limited only by measurable fluorescence and/or change thereof responsive to protein contact or interaction. One non-limiting polymer can be a green fluorescent protein, as described below. Various other polymers/biopolymers useful in the present context would be understood by those skilled in the art made aware of this invention.

BRIEF DESCRIPTION OF THE DRAWINGS

FIGS. 6C-D. C.) Chemical structure of cationic gold nanoparticles (NP1-NP14). The nanoparticles highlighted with yellow and blue were used for low and high detection limit, respectively, with green used for both. D) Schematic illustration of the competitive binding between protein and quenched nanoparticle-GFP complexes leading to the fluorescence turn on.

FIGS. 6A-B. Structure, absorbance and fluorescence spectra of GFP in 5 mM sodium phosphate buffer, pH 7.40.

FIG. 9. Fluorescence response (ΔI) patterns of the GFP-NP sensor array (NP1-NP14) against various proteins at $A_{280}$=0.005. Each value is an average of six parallel measurements.

FIG. 10. Fluorescence response (ΔI) patterns of the GFP-NP sensor array (NP1-NP14) against various proteins at $A_{280}$=0.0005. Each value is an average of six parallel measurements.

FIG. 11. Well separated fluorescence response pattern of 11 different proteins at $A_{280}$=0.005 using three sets of GFP-nanoparticle (NP7, NP12, NP14) combinations.

FIG. 12. Fluorescence response (ΔI) patterns of the nanoparticle-GFP conjugates (NP1, NP2, NP4, NP7, NP12, and NP14) in the presence of various proteins at identical absorbance value of 0.0005. Each value is an average of six parallel measurements.

FIG. 13A. Gold nanoparticle/fluorescent polymer conjugates deposited on glass demonstrating chip-based protein sensing.

DETAILED DESCRIPTION OF CERTAIN EMBODIMENTS

The "chemical nose/tongue" approach provides an alternative for the sensing protocols that use exclusive analyte-receptor binding pairs as its basis. In this strategy, a sensor array featuring selective receptors, as opposed to "lock-key" specific recognition, is used for analyte detection. Strategically, the array is able to present chemical diversity to respond differentially to a variety of analytes. Over the past few years, this approach has been used to detect a wide range of analytes, including metal ions, volatile agents, aromatic amines, amino acids and carbohydrates. There have been preliminary studies into the application of this strategy to protein sensing, including Hamilton's porphyrin-based sensors, which are used to identify four metal- and non-metal-containing proteins, and Anslyn's use of 29 botanic acid-containing oligopeptide functionalized resin beads to differentiate five proteins and glycoproteins through an indicator-uptake colorimetric analysis.

The first key challenge for the development of effective protein sensors is the creation of materials featuring appropriate surface areas for binding protein exteriors, coupled with the control of structure and functionality required for selectivity. As shown herein, nanoparticles provide versatile scaffolds for targeting biomacromolecules that have sizes commensurate with proteins, a challenging prospect with small molecule-based systems. Moreover, the self-assembled monolayer on these systems allows facile tuning of a range of surface properties in a highly divergent fashion, enabling diverse receptors to be rapidly and efficiently produced. For example, charged ligand-protected clusters can effectively recognize the protein surface through complementary electrostatic and hydrophobic interactions. The second challenge in protein sensing is the transduction of the binding event. The present strategy is to use a particle surface for protein recognition, with displacement of a fluorophore generating the output.

Figure 1A:
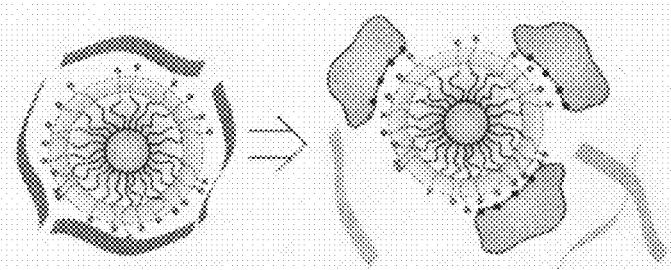
FIGS. 1A-B. Fluorophore displacement protein sensor array. A, Displacement of quenched fluorescent polymer (dark green strips, fluorescence off; light green strips, fluorescence on) by protein analyte (in blue) with concomitant restoration of fluorescence. The particle monolayers feature a hydrophobic core for stability, an oligo(ethylene glycol) layer for biocompatibility, and surface charged residues for interaction with proteins. B, Fluorescence pattern generation through differential release of fluorescent polymers from gold nanoparticles. The wells on the microplate contain different nanoparticle-polymer conjugates, and the additions of protein analytes produce a fingerprint for a given protein.
Figure 1B:
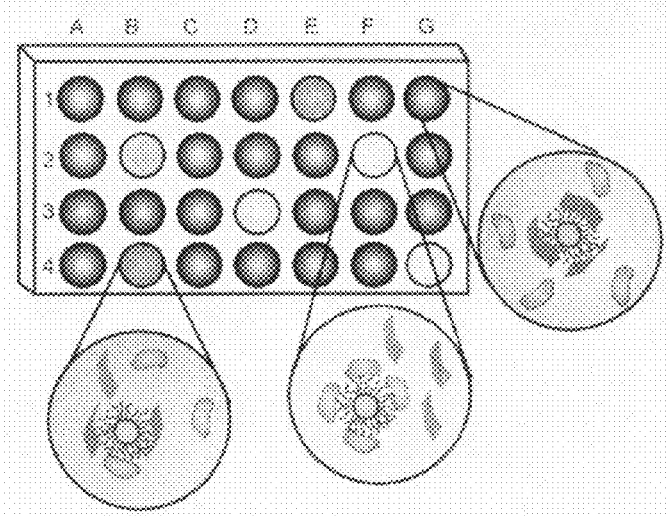

As depicted in FIG. 1A, the nanoparticles associate with charge-complementary fluorescent polymers to produce quenched complexes. The subsequent binding of protein analytes displaces the dyes, regenerating the fluorescence. By modulating the nanoparticle-protein and/or nanoparticle-polymer association, distinct signal response patterns can then be used to differentiate the proteins (FIG. 1B). The fluorescent indicator displacement assay does not require special or custom instrumentation and its sensitivity (due in large part to the high surface area provided by the nanoparticles) facilitates protein detection.

Demonstrating certain representative embodiments, a sensor array containing six non-covalent gold nanoparticle-fluorescent polymer conjugates was devised to detect, identify and quantify protein targets. The polymer fluorescence is quenched by gold nanoparticles; the presence of proteins disrupts the nanoparticle-polymer interaction, producing distinct fluorescence response patterns. These patterns are highly repeatable and are characteristic for individual proteins at nanomolar concentrations, and can be quantitatively differentiated by linear discriminant analysis (LDA). Based on a training matrix generated at protein concentrations of an identical ultraviolet absorbance at 280 nm ($A280=0.005$), LDA, combined with ultraviolet absorbance measurements, successfully identified 52 unknown protein samples (seven different proteins) with an accuracy of 94.2%. Such results demonstrate the construction of novel nanomaterial-based protein detector arrays and for applications in medical diagnostics.

Figure 2A:
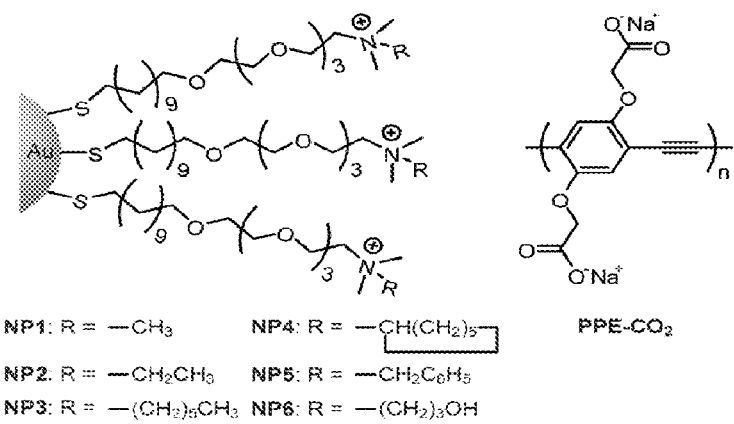
FIGS. 2A-B. Structural features of nanoparticles, polymer transducer and target analytes. A, Chemical structure of cationic gold nanoparticles (NP1-NP6) and anionic fluorescent polymer PPE-$CO_2$ (m≈12, where in refers to the number of repeated units in the polymer). B, Surface structural feature and relative size of seven proteins and the nanoparticles used in the sensing study. Colour scheme for the proteins: nonpolar residues (grey), basic residues (blue), acidic residues (red) and polar residues (green).
Figure 2B:
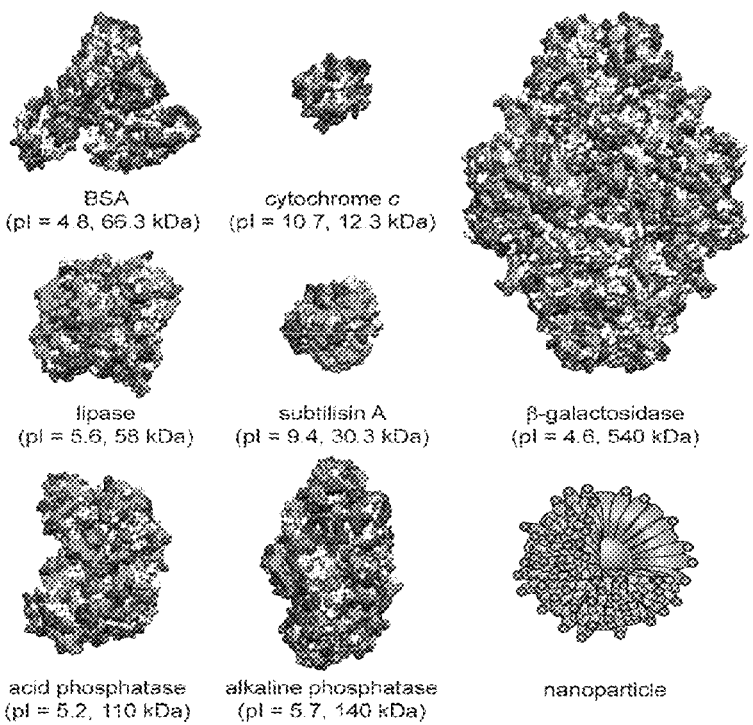

More specifically, six readily fabricated structurally related cationic gold nanoparticles (NP1-NP6) were employed to create protein sensors (FIG. 2A). These particles serve as both selective recognition elements as well as quenchers for the fluorescent polymer. Gold rather than other potential core materials (such as silver) was chosen because of its extraordinary stability; in particular its resistance to exchange by amines (for example, lysine residues) and strong quenching ability. The nanoparticle end groups carry additional hydrophobic, aromatic or hydrogen-bonding functionality engineered to tune nanoparticle-polymer and nanoparticle-protein interactions. For the fluorescent transduction element, a highly fluorescent poly(p-phenyleneethynylene) (PPE) derivative, PPE-CO2, was used as a fluorescence indicator. Seven proteins with diverse structural features including molecular weight and isoelectric point (pI) were used as the target analytes (FIG. 2B). Using these components, a competent sensor array was devised, rendering distinct fluorescence response fingerprints for individual proteins. LDA was performed to identify the protein patterns with a high degree of accuracy.

Figure 3:
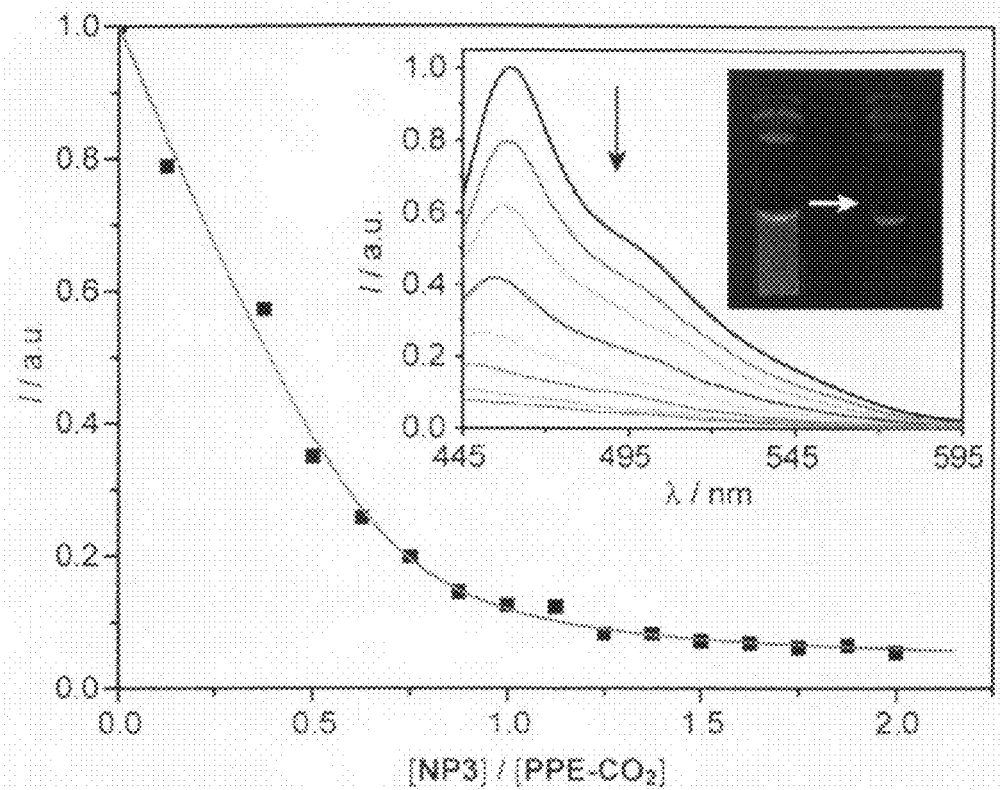
FIG. 3. Fluorescence intensity changes for PPE-$CO_2$ (100 nM) at 465 nm on addition of cationic NP3. To eliminate the absorption effect of the gold core, the fluorescence intensity was calibrated in the presence of relevant concentrations of tetra(ethyleneglycol)-functionalized gold nanoparticles, which do not associate with PPE-$CO_2$. The inset shows the fluorescence spectra and the images of PPE-$CO_2$ solution before and after addition of NP3. The arrow in the inset indicates the direction of spectral changes.

Fluorescence titration was first conducted to assess the complexation between anionic $PPE-CO_2$ and cationic gold nanoparticles NP1-NP6. The intrinsic fluorescence of $PPE-CO_2$ was significantly quenched and slightly blue-shifted on addition of all nanoparticles (FIG. 3 for NP3; comparable data for the other nanoparticles not shown). The absorption effect of gold cores was obtained through control experiments using neutral particles, and the normalized fluorescence intensities of PPE-CO2 at 465 nm were subsequently plotted versus the ratio of nanoparticle to polymer. The complex stability constants (Ks) and association stoichiometries (n) were obtained through nonlinear least-squares curve-fitting analysis (Table 1). Complex stabilities vary within approximately one order of magnitude ($\Delta\Delta G \approx 6$ kJ mol-1), and the binding stoichiometry ranges from 0.8 for NP6 to 2.9 for NP2. These observations indicate that the subtle structural changes of nanoparticle end groups significantly affect their affinity for the polymer. Significantly, all particle-polymer conjugates were optically transparent over the concentration range studied.

Once the different binding characteristics of $PPE-CO_2$, with NP1-NP6 were established, the particle-polymer conjugates were used to sense proteins. The proteins were chosen to have a variety of sizes and charges, with pI of the seven proteins varying from 4.6 to 10.7 and molecular weights ranging from 12.3 to 540 kDa. Within this set there were several pairs of proteins having comparable molecular weights and/or pI values, providing a challenging testbed for protein discrimination. In the initial sensing study, 200 µl of PPE-CO2 (100 nM) and stoichiometric nanoparticles NP1-NP6 (the stoichiometric values were taken from Table 1) were loaded onto 96-well plates for recording the initial fluorescence intensities at 465 nm. Under these conditions, it is estimated that >80% of polymer is bound to the nanoparticles, based on the binding constants listed in Table 1, allowing fluorescent enhancement through subsequent displacement.

TABLE 1

Binding constants ($logK_s$) and binding stoichiometries (n) between polymer $PPE-CO_2$ and various cationic nanoparticles (NP1-NP6) as determined from fluorescence titration.

| Nanoparticle | $K_S$ ($10^8$ $M^{-1}$) | $-\Delta G$ (kJ $mol^{-1}$) | n |
|---|---|---|---|
| NP1 | 3.0 | 48.4 | 2.0 |
| NP2 | 2.1 | 47.5 | 2.9 |
| NP3 | 1.7 | 47.0 | 1.5 |
| NP4 | 21.0 | 53.2 | 1.8 |
| NP5 | 3.6 | 48.8 | 2.4 |
| NP6 | 25.0 | 53.6 | 0.8 |

Figure 4A:
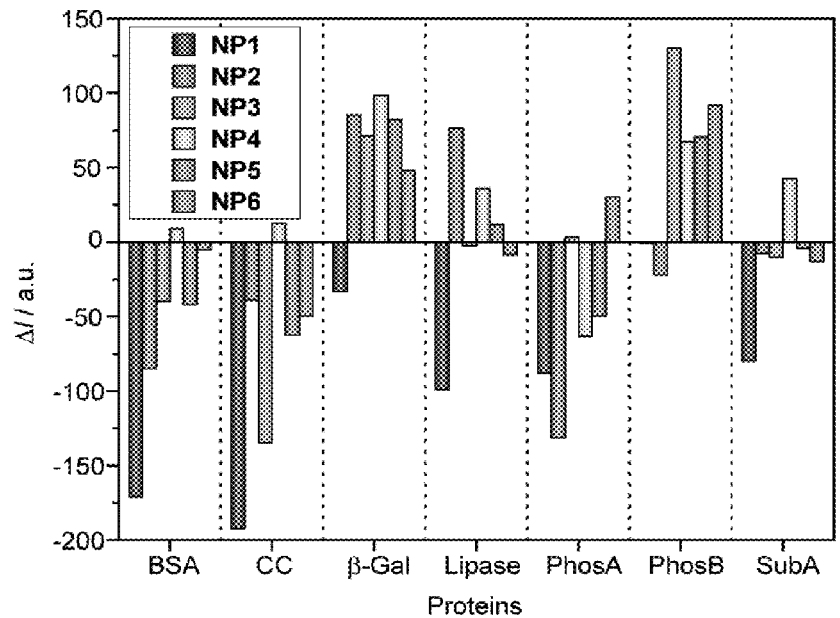
FIGS. 4A-B. Array-based sensing of protein analytes at 5 μM. A, Fluorescence response (ΔI) patterns of the NP-PPE sensor array (NP1-NP6) against various proteins (CC, cytochrome c; β-Gal, β-galactosidase; PhosA, acid phosphatase; PhosB, alkaline phosphatase; SubA, subtilisin A). Each value is an average of six parallel measurements B, Canonical score plot for the first two factors of simplified fluorescence response patterns obtained with NP-PPE assembly arrays against 5 μM proteins. The canonical scores were calculated by LDA for the identification of seven proteins. The 95% confidence ellipses for the individual proteins are also shown.

As illustrated in FIG. 4A, addition of aliquots of protein (5 μM) resulted in a variety of fluorescence responses. By contrast, the addition of proteins (5 μM) into PPE-CO$_2$ (100 nM) induced only marginal fluorescence changes, confirming the disruption of nanoparticle-PPE-CO$_2$ interactions by proteins. BSA, β-galactosidase, acid phosphatase and alkaline phosphatase induced different levels of fluorescence increase, and cytochrome c, the only metal-containing protein, further attenuated the fluorescence of the systems; presumably through an energy or electron transfer process. Lipase and subtilisin A had smaller, but still significant, fluorescence changes for most nanoparticle-PPE systems. Notably, each protein possesses a unique response pattern. Without limitation to any one theory or mode of operation, such an outcome is reasonable, because their interaction with the protein-detecting array may be dependent on surface characteristics such as the distribution of hydrophobic, neutral and charged amino-acid residues. For each protein, its fluorescence responses were tested against the six nanoparticle-PPE assemblies six times, generating a 6×6×7 matrix.

Figure 4B:
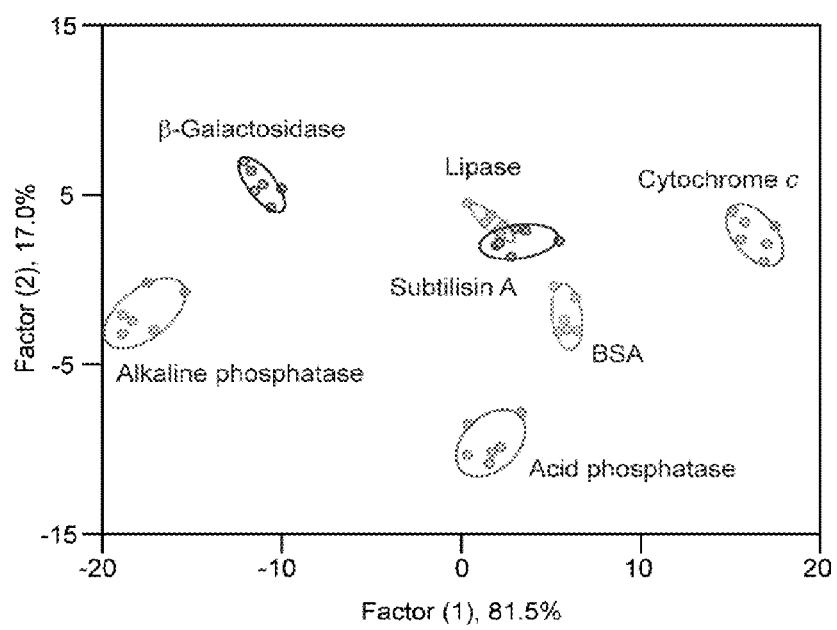

The raw data obtained were subjected to LDA to differentiate the fluorescence response patterns of the nanoparticle-PPE systems against the different protein targets. LDA is used in statistics to recognize the linear combination of features that differentiate two or more classes of object or event. It can maximize the ratio of between-class variance to the within-class valiance in any particular data set, thereby enabling maximal separability. This analysis reduced the size of the training matrix (6 nanoparticles×7 proteins×6 replicates) and transformed them into canonical factors that are linear combinations of the response patterns (5 factors×7 proteins×6 replicates). The five canonical factors contain 96.4%, 1.9%, 0.8%, 0.6% and 0.3% of the variation, respectively. The first two factors were visualized in a two-dimensional plot as presented in FIG. 4B. In this plot, each point represents the response pattern for a single protein to the nanoparticle-PPE sensor array.

The canonical fluorescence response patterns of 5 μM proteins against the nanoparticle-PPE sensor array are clustered to seven distinct groups according to the protein analyte, with no overlap between the 95% confidence ellipses. This result demonstrates that LDA allows the discrimination of very subtle differences in protein structure. Moreover, LDA provides in-depth quantitative analysis of the fluorescence responses of protein analytes. The assignment of the individual case was based on its Mahalanobis distances to the centroid of each group in a multidimensional space, as the closer a case is to the centroid of one group, the more likely it is to be classified as belonging to that group. The 42 training cases (7 proteins×6 replicates) can be totally correctly assigned to their respective groups using LDA, giving 100% accuracy. Furthermore, another 56 protein samples were prepared randomly and used as unknowns in a blind experiment, where the individual performing the analysis did not know the identity of the solutions. During LDA analysis, the new cases were classified to the groups generated through the training matrix according to their Mahalanobis distances. Of 56 cases, 54 were correctly classified, affording an identification accuracy of 96.4%. This result confirms not only the reproducibility of the fluorescence patterns, but also the feasibility of practical application of such a nanoparticle-conjugated polymer sensor array in detection and identification of proteins.

Real-world applications, however, require identification of proteins at varying concentrations. Varying protein concentrations would be expected to lead to the drastic alteration of fluorescence response patterns for the proteins, making identification of proteins with both unknown identity and concentration challenging. To enable the detection of unknown proteins, a protocol was designed combining LDA and ultraviolet (UV) absorbance measurements. In this approach, a set of fluorescence response patterns were generated at analyte protein concentrations that generated a standard UV absorption value at 280 nm ($A_{280}$=0.005), the lowest concentration for which the proteins could be substantially differentiated using the given sensor array followed by LDA. Therefore, this concentration could also be treated as the detection limit of this assay, with molar concentrations ranging from 4 nM for β-galactosidase to 215 nM for cytochrome c (see FIG. 5 for other proteins). In this unknown identification protocol, the $A_{280}$ value of the protein was determined, and an aliquot subsequently diluted to $A_{280}$=0.005 for recording the fluorescence response pattern against the NP-PPE sensing array. Once the identity of the protein was established by LDA, its initial concentration could be determined from the initial $A_{280}$ value and corresponding molar extinction coefficient ($\epsilon_{280}$) according to the Beer-Lambert law.

Figure 5A:
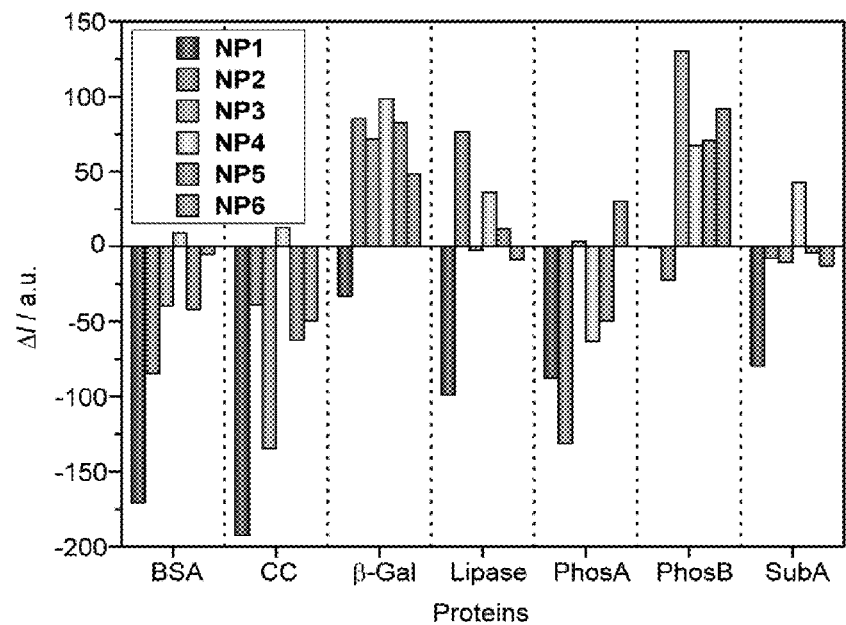
FIG. 5. Array-based sensing of protein analytes with identical absorbance at 280 nm. A, Fluorescence response (ΔI) patterns of the NP-PPE sensor array. B, Canonical score plot for the first two factors of simplified fluorescence response patterns obtained with NP-PPE assembly arrays against proteins with identical absorption values of A=0.005 at 280 nm. The canonical scores were calculated by LDA for the identification of seven proteins, with 95% confidence ellipses for the individual proteins shown. [BSA]=110 nM; [cytochrome c]=215 nM; [β-galactosidase]=4 nM; [lipase]=90 nM; [acid phosphatase]=20 nM; [alkaline phosphatase]=80 nM; [Subtilisin A]=190 nM.
Figure 5B:
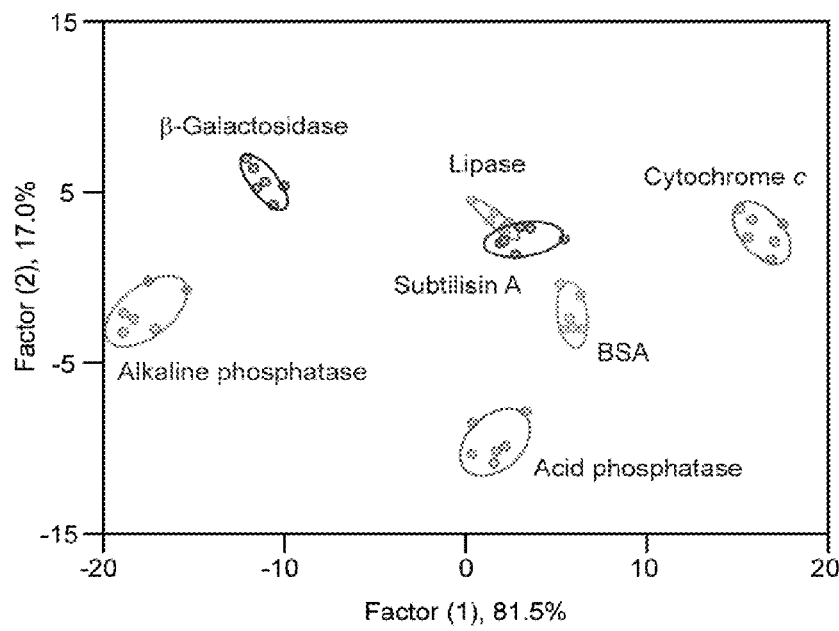

The fluorescence response patterns where the protein concentration is $A_{280}$=0.005 are distinctly different from those generated from 5 μM of proteins, but retain a high degree of reproducibility (FIG. 5A). As before, LDA accurately differentiates the protein patterns. As shown in FIG. 5B, the canonical fluorescence response patterns display excellent separation, except for a minor overlap between lipase and subtilisin A. According to the Jack-knifed classification matrix (the classification matrix with cross-validation) in the LDA results, only one subtilisin A sample is misclassified, affording a classification accuracy of 97.6% (41/42). As a control, analogous analyses were performed using polymer ([PPE-CO2]=100 nM) in the absence of nanoparticles. These studies show that the polymer itself can only substantially differentiate cytochrome c, the metalloprotein, from the other proteins. For the other six proteins, only 50% classification accuracy is obtained on the basis of six replicates of measurement, only modestly higher than the statistical possibility (that is, 17%). A further in-depth examination on the classification accuracy of the polymer in the absence and presence of individual nanoparticles revealed that the particle-polymer complexes generally afforded better differentiation abilities than the polymer alone, demonstrating the role of the nanoparticle in providing the differentiation between proteins required for effective sensing.

A series of unknown protein solutions were subsequently used for quantitative detection. To facilitate solution preparation and UV measurement, the unknown proteins were prepared at varying concentrations (between 120 nM and 50 μM). In principle, lower concentrations can also be used because the detection limit of this method is nanomolar. The unknown protein solutions were submitted to the testing procedures, including determination of $A_{280}$, dilution of solution to $A_{280}$=0.005, fluorescence response recording against the sensor array, and LDA. Of the 52 unknown protein samples, 49 samples were correctly identified, affording an identification accuracy of 94.2%. In addition, the protein concentration was assessed generally within ±5% once it was identified. This result unambiguously manifests that a sensor array of this invention can be used for both the identification and quantification of protein analytes.

As demonstrated above, that the assemblies of gold nanoparticles with fluorescent PPE polymer provide efficient sensors of proteins, achieving both the detection and identification of analytes. This strategy exploits the size and tunability of the nanoparticle surface to provide selective interactions with proteins, and the efficient quenching of fluorophores by the metallic core to impart efficient transduction of the binding event. Through application of LDA, fluorescence changes were used to identify and quantify proteins in a rapid, efficient and general fashion. The robust characteristics of the nanoparticle and polymer components, coupled with diversity of surface functionality that can be readily obtained using nanoparticles, make this array approach a technique which can be used for biomedical diagnostics.

Figure 6C:
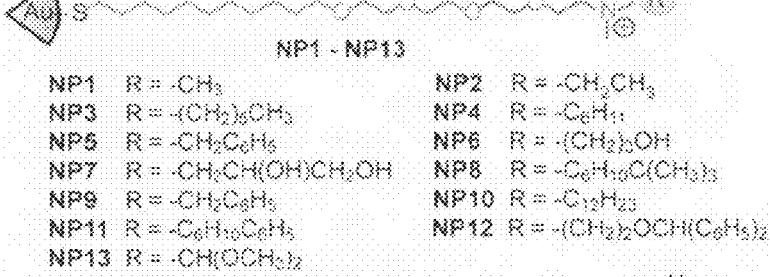
Figure 6D:
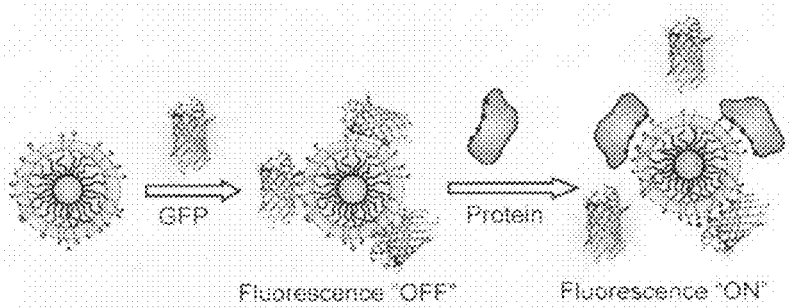

Various other embodiments of this invention can utilize a biopolymer component to provide lowered limits of detection coupled with excellent biocompatibility. Demonstrating this approach, with reference to examples 6-11, an array of green fluorescent protein (GFP)-nanoparticle complexes was prepared to illustrate detection and identification of a wide range of proteins. The biocompatibility of a nanoparticle and GFP complex promotes detection without any effect on target protein conformation. GFP is a beta-barrel shaped marker protein that is negatively charged at physiological conditions (3.0×4.0 nm, MW=26.9 kDa, pH 7.4, pI=5.92), with an excitation peak at 490 nm and emission peak at 510 nm (FIGS. 6A-B). Negatively charged, GFP complexes with cationic gold nanoparticles, quenching its fluorescence. Subsequent displacement of the GFP from the particle by an analyte protein regenerates GFP fluorescence. For purpose of demonstration, fourteen cationic gold nanoparticles (NP1-NP14) were synthesized. While all were provided with cationic charge, the nanoparticles were varied with respect to hydrophobicity, aromaticity, and hydrogen bonding functionality (FIG. 6C). In the presence of protein analytes/targets, GFP-nanoparticle interactions are disrupted to generate distinct fluorescent signal patterns. The affinity for such GFP-nanoparticle complexes can then be used to detect and/or identify protein analytes (FIG. 6D).

Figure 7:
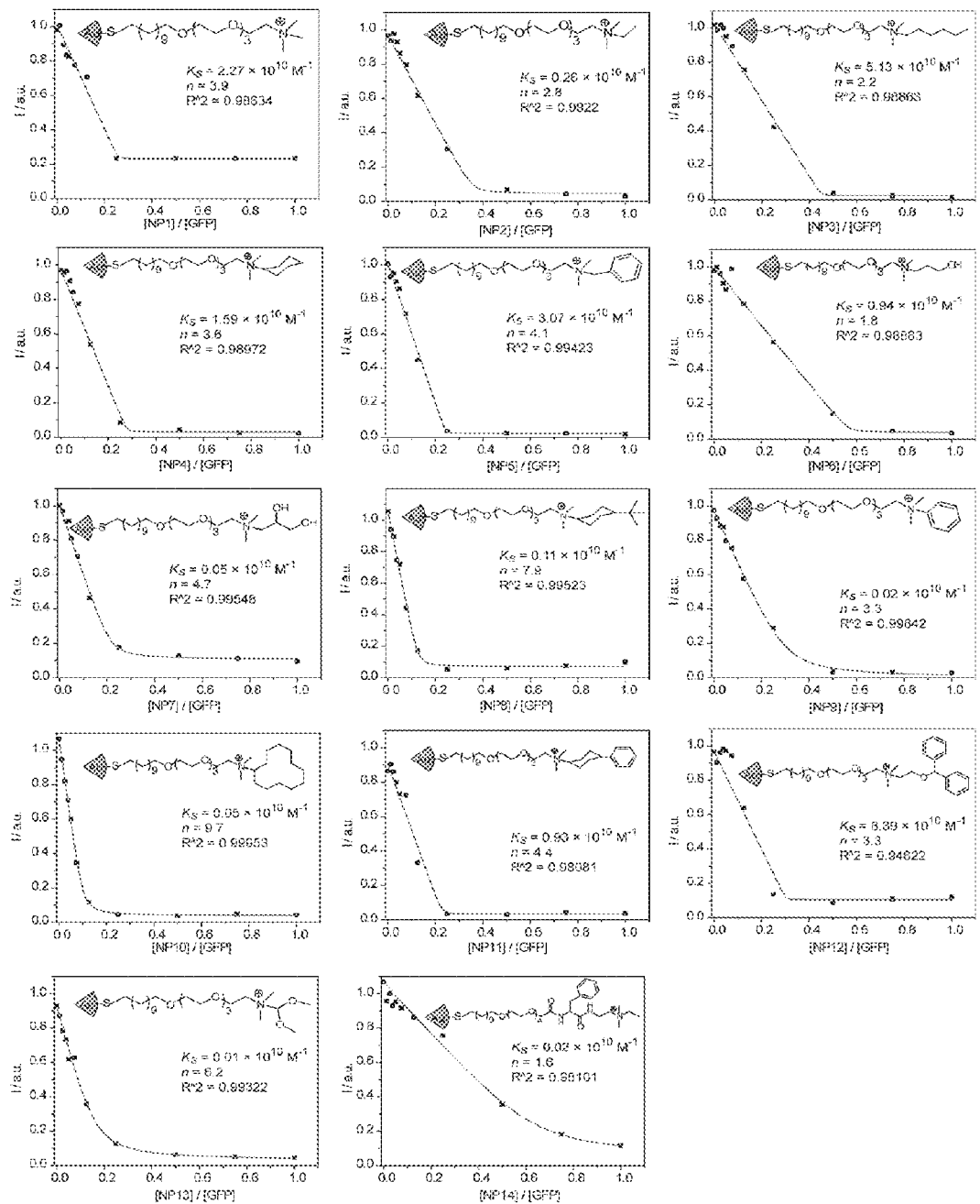
FIG. 7. Fluorescence titration curves for the complexation of GFP with 14 different cationic gold nanoparticles NP1-NP14. The changes of fluorescence intensity at 510 nm were measured following the addition of cationic nanoparticles (0-100 nM) with an excitation wavelength of 475 nm. The red solid lines represent the best curve fitting using the model of single set of identical binding sites.

The binding ratio between GFP and nanoparticles (NP1-NP14) was optimized using fluorescence titration. GFP fluorescence was significantly quenched for all nanoparticles, and the change of fluorescence intensity against increasing nanoparticle concentrations was plotted (FIG. 7), using a non-interacting gold nanoparticle (e.g. PEG-NP) as a control to compensate for particle absorption. Complex stability constants ($K_S$) and association stoichiometries (n) were obtained through nonlinear least-squares curve-fitting analysis (Table 3, below). (You, C. C., et al., *J. Am. Chem. Soc.* 2005, 127, 12873.) The variation in complex stabilities (AG, −62.35 to −45.66 kJ mol$^{-1}$) and the binding stoichiometry (m, 9.7 to 1.6) demonstrate an end group effect in nanoparticle-protein affinity.

TABLE 2

Analyte proteins and concentrations used in study

| Proteins | $\epsilon_{280}$ ($M^{-1}$ cm$^{-1}$) | $A_{280}$ 0.005 | $A_{280}$ 0.0005 |
|---|---|---|---|
| Bovine serum alb. (BSA) | 46860 | 107 | 10.7 |
| Acid phosphatase (PhosA) | 257980 | 19 | 1.9 |
| α-amylase (α-Am) | 130000 | 38 | 3.8 |
| β-galactosidase (β-Gal) | 1128600 | 4 | 0.4 |
| Subtilisin A (SubA) | 26030 | 192 | 19.2 |
| Hemoglobin (Hem) | 125000 | 40 | 4.0 |
| Human serum alb. (HSA) | 37800 | 132 | 13.2 |
| Alk. phosphatase (PhosB) | 62780 | 80 | 8.0 |
| Myoglobin (Myo) | 13940 | 359 | 35.9 |
| Lipase (Lip) | 54350 | 92 | 9.2 |
| Histone (His) | 3840 | 1302 | 130 |

Once the optimal binding ratios were determined, eleven target proteins with diverse sizes and charges were used to demonstrate the method (Table 2). In this protocol, linear discriminant analysis (LDA) and UV absorbance measurements were used to test efficiency. As all the proteins have characteristic absorption maxima at 280 nm, standard absorbances ($A_{280}$=0.005 and 0.0005) were used for target analytes. To prove the capability of this array sensor, fluorescence response was tested against the corresponding GFP-nanoparticle complexes using six duplicates.

Figure 8A:
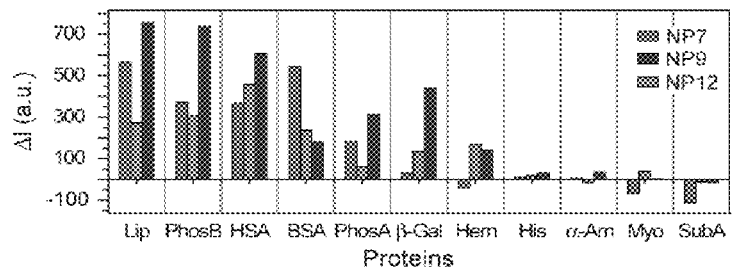
FIGS. 8A-C. Fluorescence response (ΔI) patterns of the nanoparticle-GFP adduct (NP7, NP9 and NP12) in the presence of various proteins at a fixed absorbance value of 0.005 (average of six measurements). Canonical score plot for the fluorescence patterns as obtained from LDA against 11 protein analytes at fixed absorbance values: B) $A_{280}$=0.005 (NP7, NP9 and NP12) and C) $A_{280}$=0.0005 (NP1, NP2, NP4, NP7, NP12 and NP14), with 95% confidence ellipses shown for each.
Figure 8B:
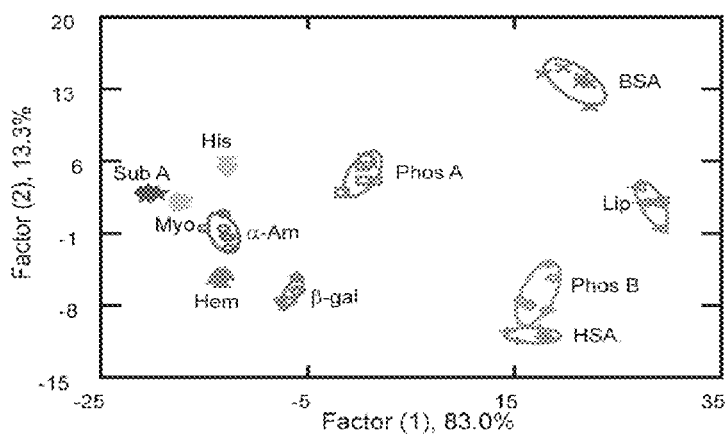

Addition of proteins into GFP-nanoparticle complexes at the same absorbance value ($A_{280}$=0.005) resulted in unique fluorescence response patterns for each protein (FIG. 8). At $A_{280}$=0.005 three GFP-nanoparticle complexes (NP7, NP9, NP12) afford an optimal classification of 100% accuracy (3 factors×11 proteins×6 replicates, Jackknifed classification matrix=100%) (FIGS. 8A-B). This efficiency was mirrored in our unknown studies, where 48 unknown protein samples from the 11 target analytes were randomly prepared and identified with 100% identification accuracy (Table 8).

Figure 8C:
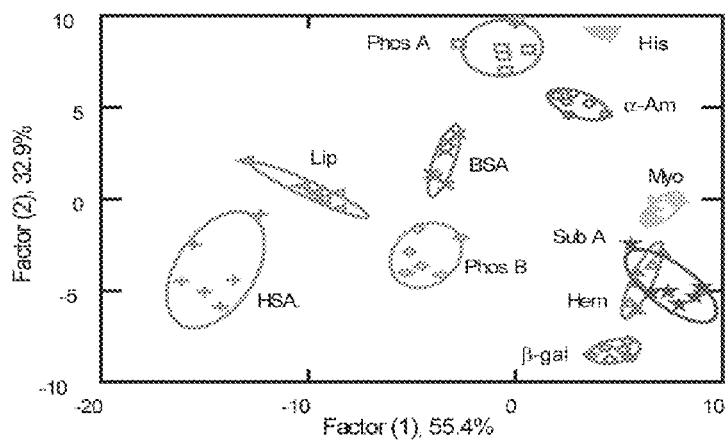

In the case of $A_{280}$=0.0005, biosensor accuracy was reduced to 70% using the same three nanoparticles. Accuracy was restored using six GFP-nanoparticle complexes (NP1, NP2, NP4, NP7, NP12, NP14), obtaining 98% accuracy (6 factors×11 proteins×6 replicates, Jackknifed classification matrix=98%) (FIG. 8C). For this set, 45 out of 48 unknown samples were correctly identified, affording an identification accuracy of 94% (Table 9) with a detection limit as low as 400 picomolar for β-galactosidase.

Reference is made to examples 6-11 which demonstrate a GFP-nanoparticle array biosensor can effectively identify a wide range of proteins at nano/picomolar concentrations. The competitive complexation between GFP and analyte proteins with nanoparticles makes this system comparable to natural protein-protein interactions, providing potential for further optimization via engineering of both the synthetic and biological components.

Figure 13B:
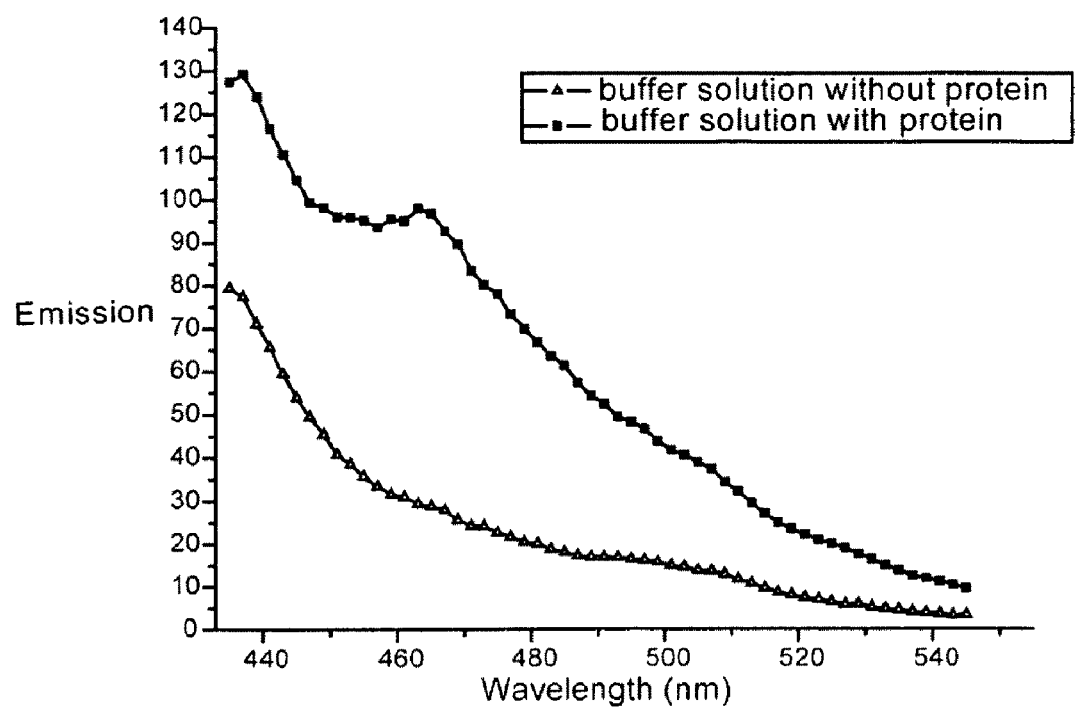
FIG. 13B. Preliminary results obtained using gold nanoparticle/fluorescent polymer conjugates deposited on glass demonstrating chip-based protein sensing and, in particular, efficient detection of Bovine Serum Albumin (BSA).

Regardless of the identity of any nanoparticle, fluorophore polymer or analyte, this invention can be embodied by a matrix including an array of a plurality of the same or different sensor complexes on, connected with and/or coupled to a solid substrate—such as a matrix as can be utilized as or a part of a chip-based sensor, kit or related sensor apparatus for analyte detection and/or identification. For purpose of illustration only, a representative matrix can be fabricated as illustrated in FIG. 13A. For example, a silicon wafer or suitable substrate material (e.g., with a hydroxylated surface) can be thiol-functionalized with an appropriate silane reagent, then coupled to gold nanoparticles. Optional ligand (e.g., citrate) protection can be removed and/or exchanged for a cationic ligand component, of the type described herein, for subsequent non-covalent fluoropolymer binding. Microspotter apparatus and techniques can be used for surface and/or nanoparticle functionalization and subsequent polymer absorption. Such a surface-based protocol and assembly precludes premixing polymer with particle. Contact with a fluid medium (e.g., a biofluid possibly containing an analyte of interest) can be simply introduced to such a chip matrix, with fluorescence and/or change thereof recorded using either plate-reader technology or a suitable CCD camera. Emission spectrum change of such a sensor, on contact with a representative protein analyte, is graphically illustrated in FIG. 13B.

EXAMPLES OF THE INVENTION

The following non-limiting examples and data illustrates various aspects and features relating to the methods and/or articles of the present invention, including the detection and identification of unknown proteins. In comparison with the prior art, the present methods and/or articles provide results and data which are surprising, unexpected and contrary thereto. While the utility of this invention is illustrated through the use several nanoparticulate sensor complexes and molecular components which can be used to therewith in the context of certain proteins, it will be understood by those skilled in the art, that comparable results are obtainable with various other nanoparticles and fluorophore components in the detection/identification of other proteins (e.g., biomarkers, etc.), as are commensurate with the scope of this invention.

With reference to examples 1-5, carboxylate-substituted PPE (PPE-CO2) was synthesized according to a known procedure. (Bunt, U. H. F. Synthesis and structure of PAEs. *Adv. Polym. Sci.* 177, 1-52 (2005); Zheng, J. & Swager, T. M. Poly(arylene ethynylene)s in chemosensing and biosensing. *Adv. Polym. Sci.* 177, 151-179 (2005); Kim, 1-B, Dunkhorst, A., Gilbert, J. & Bunz, U. H. F. Sensing of lead ions by a carboaxlate-substituted PPE: multivalency effects. *Macromolecules* 38, 4560-4562 (2005).) The weight- and number-averaged molecular weights of the polymer are 6,600 and 3,500, respectively. The polydispersity index and degree of polymerization of the conjugated polymer are 1.88 and 12, respectively. Thiol ligands bearing ammonium end groups were synthesized through the reaction of 1,1,1-triphenyl-14, 17,20,23-tetraoxa-2-thiapentacosan-25-yl methanesulphonate with corresponding substituted N,N-dimethylamines followed by deprotection in the presence of trifluoroacetic acid and triisopropylsiane. Subsequent place-exchange reaction with pentanethiol-coated gold nanoparticles (d≈2 nm) resulted in cationic gold nanoparticles NP1-NP6 in high yields. (See, example 5, below, and Brust, M., Walker, M., Bethell, D, Schiffrin, D. J. & Whyman, R. Synthesis of thiol-derivatised gold nanoparticles in a two-phase liquid-liquid system. *J. Chem. Soc., Chem. Commun.* 801-802 (1994).) $^1$H NMR spectroscopic investigation revealed that the place-exchange reaction proceeds almost quantitatively and the coverage of cationic ligands on the nanoparticles is near unity.

Bovine serum albumin, cytochrome c (from horse heart), β-galactosidase (from *E. coli*), lipase (from *Candida rugosa*), acid phosphatase (from potato), alkaline phosphatase (from bovine intestinal mucosa) and subtilisin A (from *Bacillus licheniformis*) were purchased from Sigma-Aldrich and used as received. Phosphate buffered saline (PBS, pH 74, ×1) was purchased from Invitrogen and used as the solvent throughout the fluorescence assays.

Example 1

In the fluorescence titration study, fluorescence spectra were measured in a conventional quartz cuvette (10×10×40 mm) on a Shimadzu RE-5301 PC spectrofluorophotometer at room temperature (~25° C.). During the titration, 2 mL of PPE-CO$_2$ (100 nM) was placed in the cuvette and the initial emission spectrum was recorded with excitation at 430 nm. Aliquots of a solution of PPE-CO$_2$ (100 nM) and nanoparticles were subsequently added to the solution in the cuvette. After each addition, a fluorescence spectrum was recorded. The normalized fluorescence intensities calibrated by respective controls (tetra(ethylene glycol)-functionalized neutral nanoparticle with the same core) at 465 nm were plotted against the molar ratio of nanoparticle to PPE-CO$_2$. Nonlinear least-squares curve-fitting analysis was conducted to estimate the complex stability as well as the association stoichiometry using a calculation model in which the nanoparticle is assumed to possess n equivalent and independent binding sites.

Example 2

In the protein sensing study, fluorescent polymer PPE-CO$_2$ and stoichiometric nanoparticles NP1-NP6 (determined by fluorescence titration; Table 1) were placed into six separate glass vials and diluted with PBS buffer to afford mixture solutions where the final concentration of PPE-CO$_2$ was 100 nM. Then, each solution (200 μl) was respectively loaded into a well on a 96-well plate (300 μl Whatman Glass Bottom microplate) and the fluorescence intensity value at 465 nm was recorded on a Molecular Devices SpectraMax M5 micro plate reader with excitation at 430 nm. Subsequently, 10 μl of protein stock solution (105 μM) was added to each well (final concentration 5 μM), and the fluorescence intensity values at 465 nm were recorded again. The difference between two reads before and after addition of proteins was treated as the fluorescence response.

Example 3

This process was repeated for seven protein targets to generate six replicates of each. Thus, the seven proteins were tested against the six-nanoparticle array (NP1-NP6) six times, to give a 6×6×7 training data matrix. The raw data matrix was processed using classical LDA in SYSTAT (version 11.0). Similar procedures were also performed to identify 56 randomly selected protein samples.

Example 4

In the studies featuring unknown analyte protein concentrations, the sensor array was tested against seven proteins ($A_{280}$=0.005) six times to generate the training data matrix. Fifty-two unknown protein solutions were subjected successively to UV absorption measurement at 280 nm, dilution to $A_{280}$=0.005, fluorescence response pattern recording against the sensor array, and LDA. After the protein identity was recognized by LDA, the initial protein concentration, c, was deduced from the $A_{280}$ value and corresponding molar extinction coefficient ($\epsilon_{280}$) on the basis of the Beer-Lambert law ($c=A_{280}/(\epsilon_{280}l)$). In the experimental setup, the protein samples were randomly selected from the seven protein species and the solution preparation, data collection and LDA analysis were performed by different persons.

Example 5

Synthesis of Cationic Gold Nanoparticles 4

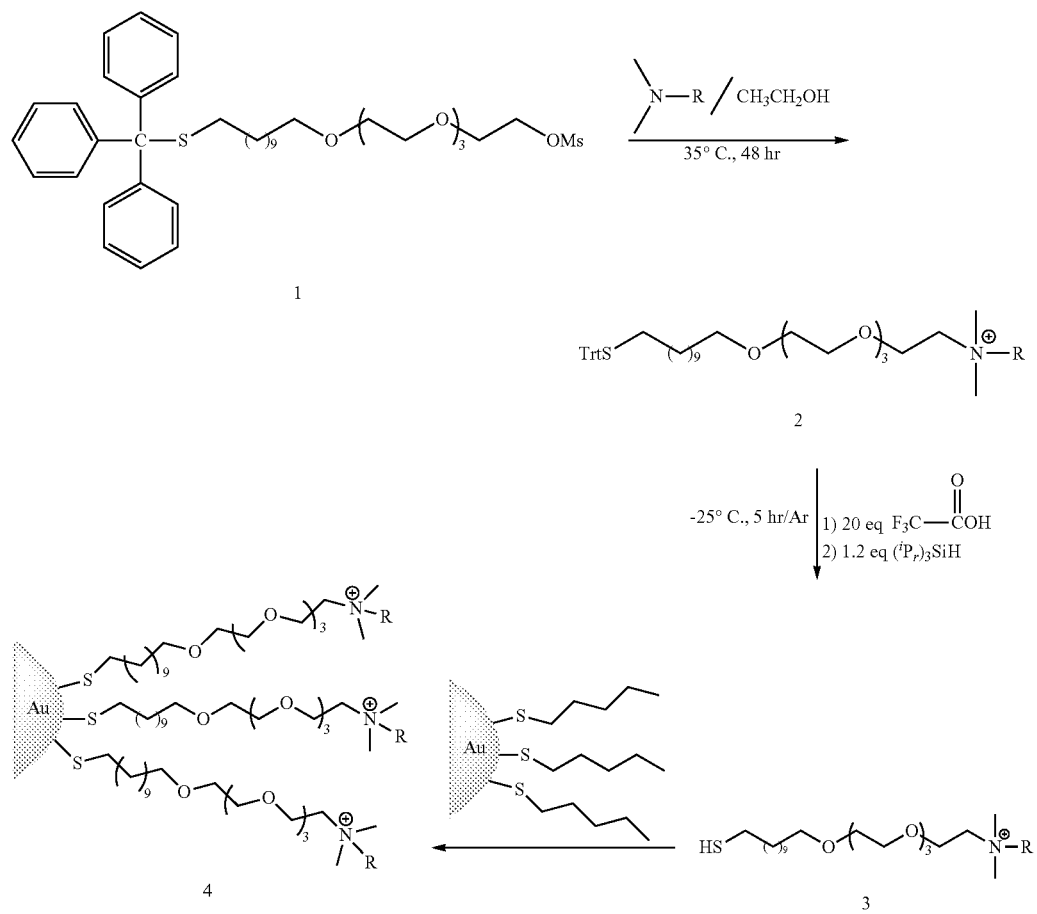

General procedure: Compound 2 bearing ammonium end groups were synthesized through the reaction of 1,1,1-triphenyl-14,17,20,23-tetraoxa-2-thiapentacosan-25-yl methanesulphonate (1) with corresponding substituted N,N-dimethylamines during 48 h at ~35° C. The trityl protected thiol ligand (2) was dissolved in dry DiChloroMethane (Methylene Chloride, DCM) and an excess of trifluoroacetic acid (TFA, ~20 equivalent) was added. The color of the solution was turned to yellow immediately. Subsequently, triisopropylsilane (TIPS, ~1.2 equivalent) was added to the reaction mixture. The reaction mixture was stirred at room temperature for ~5 h under Ar condition at room temperature. The solvent and most TFA and TIPS were distilled off under reduced pressure. The pale yellow residue was further dried in high vacuum. The product formation was quantitative and their structure was confirmed by NMR. Subsequent place-exchange reaction of compound 3 dissolved in DCM with pentanethiol-coated gold nanoparticles (d~2 nm) was carried out for 3 days at environmental temperature. Then, DCM was evaporated under reduced pressure. The residue was dissolved in a small amount of distilled water and dialyzed (membrane MWCO=1,000) to remove excess ligands, acetic acid and the other salts present with the nanoparticles. After dialysis, the particles were lyophilized to afford a brownish solid. The particles are redispersed in water and ionized water (18 MΩ-cm). $^1$H NMR spectra in $D_2O$ showed substantial broadening of the proton signals and no free ligands were observed.

The following materials and protocols were employed in conjunction with the results and data provided in examples 6-11 and with reference to FIGS. 6-12.

Materials

Green fluorescence protein (GFP) was expressed according to standard procedures using *E. coli*. The Mw and pI of the expressed GFP is 26.9 KDa and 5.92 respectively. The maximum $\lambda_{ex}$ and $\lambda_{em}$ are 490 nm and 510 nm (FIG. 6B). The analyte proteins, bovine serum albumin (BSA), acid phosphatase (PhosA, from potato), α-amylase (α-Am, from *Bacillus Licheniformis*), lipase (Lip, from *Candida Rugosa*, type VII), (β-galactosidase (β-Gal, from *Escherichia Coli*), Subtilisin A (SubA, from *Bacillus Licheniformis*), hemoglobin (Hem, from human), human serum albumin (HAS), alkaline phosphatase (Phosβ, from bovine intestinal mucosa), Histone (His, from calf thymus, type III-S) and myoglobin (Myo, from equine heart) were purchased from Sigma-Aldrich and used as received. 5 mM sodium phosphate buffer, pH 7.4 was used as a solvent throughout the experiment. Cationic nanoparticles NP1-NP6, NP9 were synthesized according to literature procedure (Rotello, et al., *Nat. Nanotech.* 2007, 2, 318) and NP7, NP8, NP10-NP14 were prepared according to the procedure described below.

Expression and Purification of GFP

Starter cultures from a glycerol stock of GFP in BL21 (DE3) was grown overnight in 50 ml of 2_YT media with 50 µl of 1000 m ampicilin (16 g tryptone, 10 g yeast extract, 5 g NaCl in 1 L water). The cultures were shook overnight at 250 rpm at 37° C. The following day, 5 ml of the starter cultures was added to a Fernbach flask containing 1 L of 2_YT and 1 ml 1000_amplicilin and shook until the $OD_{600}$=0.7. The culture was then induced by adding IPTG (1 mM final concentration) and shook at 28° C. After three hours, the cells were harvested by centrifugation (5000 rpm for 15 minutes at 4° C.). The pellet was then resuspended in lysis buffer (2 mM Imidizole, 50 mM $NaH_2PO_4$, 300 mM NaCl). The cells were lysed using a microfluidizer. Once lysed, the solution was pelleted at 15000 rpm for 45 minutes at 4° C. The supernatant was further purified using HisPur Cobalt columns from Pierce (cat. Number 89969).

Example 6

Synthesis of Ligands

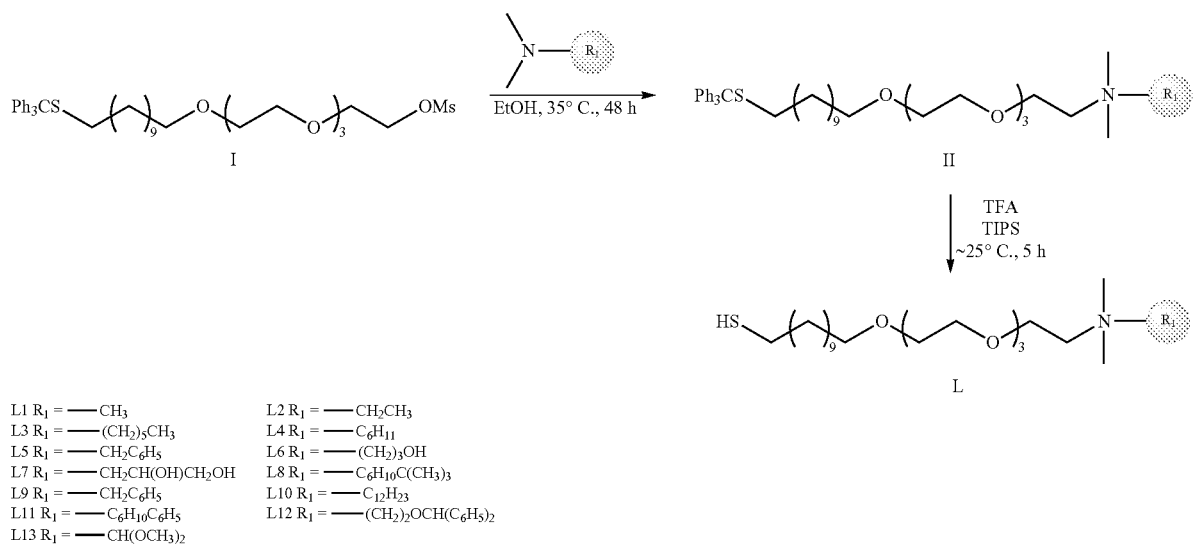

General procedure: Compound II bearing ammonium end groups were synthesized through the reaction of 1,1,1-triphenyl-14,17,20,23-tetraoxa-2-thiapentacosan-25-yl methanesulphonate (I) with corresponding substituted N,N-dimethylamines at ~35° C. for 48 h. The trityl protected thiol ligand (II) was dissolved in dry DiChloroMethane (Methylene Chloride, DCM) and an excess of trifluoroacetic acid (TFA, ~20 equivalents) was added. The color of the solution was turned to yellow immediately. Subsequently, triisopropylsilane (TIPS, ~1.2 equivalents) was added to the reaction mixture. The reaction mixture was stirred for ~5 h under Ar condition at room temperature. The solvent and most TFA and TIPS were distilled off under reduced pressure. During the process of purification of compound (L) $Ph_3CH$ was removed using hexane under sonication at warm conditions. The pale yellow residue was further dried in high vacuum. The product (L) formation was quantitative and their structure was confirmed by $^1H$ NMR. The yields were >95%.

Compound L1: $^1H$ NMR (400 MHz, $CDCl_3$, TMS): δ 3.95 (br, 2H, —$CH_2O$—), 3.70-3.58 (m, 14H, —$CH_2O$—+—$OCH_2$—($CH_2N$)—), 3.49 (t, 2H, —$CH_2N$—), 3.25 (s, 9H, —$N(CH_3)_3$), 2.90 (s, 3H, —$CH_3SO^-_3$—), 2.52 (q, 2H, —$CH_2S$—), 1.64-1.51 (m, 4H, ($SCH_2$)$CH_2$+—$CH_2(CH_2O)$—), 1.36-1.22 (m, 15H, —SH+—$CH_2$—).

Compound L2: $^1H$ NMR (400 MHz, $CDCl_3$, TMS): δ 3.94 (br, 2H, —$CH_2O$—), 3.69-3.56 (m, 14H, —$CH_2O$—+—$OCH_2$—($CH_2N$)—), 3.44 (t, 2H, —$CH_2N$—), 3.40-3.32 (m, 2H, —$NCH_2$—), 3.23 (s, 6H, —($CH_3)_2N$—), 2.78 (s, 3H, —$CH_3SO^-_3$—), 2.51 (q, 2H, —$CH_2S$—), 1.69-1.149 (m, 4H, ($SCH_2$)$CH_2$+—$CH_2(CH_2O)$—), 1.44-1.24 (m, 18H, —SH+—$CH_2$—+—($NCH_2$)$CH_3$).

Compound L3: $^1H$ NMR (400 MHz, $CDCl_3$, TMS): δ 3.95 (br, 2H, —$CH_2O$—), 3.68-3.56 (m, 14H, —$CH_2O$—+—$OCH_2$—($CH_2N$)—), 3.46 (t, 2H, —$CH_2N$—), 3.40-3.33 (m, 2H, —$NCH_2$—), 3.19 (s, 6H, —($CH_3)_2N$—), 2.87 (s, 3H, —$CH_3SO^-_3$—), 2.52 (q, 2H, —$CH_2S$—), 1.76-1.53 (m, 6H, —($NCH_2$)$CH_2$—)+($SCH_2$)$CH_2$+—$CH_2(CH_2O)$—), 1.41-1.22 (m, 21H, —SH+—($NCH_2CH_2$—)$CH_2$—)+—$CH_2$—), 0.89 (t, 3H, —$CH_3$—).

Compound L4: $^1H$ NMR (400 MHz, $CDCl_3$, TMS): δ 3.95 (br, 2H, —$CH_2O$—), 3.81-3.72 (m, 1H, $H_{Cyclo}$), 3.69-3.53 (m, 14H, —$CH_2O$—+—$OCH$—($CH_2N$)—), 3.49 (t, 2H, —$CH_2N$—), 3.11 (s, 6H, —($CH_3)_2N$—), 2.91 (s, 3H, —$CH_3SO^-_3$—), 2.52 (q, 2H, —$CH_2S$—), 2.23 (d, 2H, $H_{Cyclo}$), 1.99 (d, 2H, $H_{Cyclo}$), 1.78-1.52 (m, 4H, —($SCH_2$)$CH_2$+—$CH_2(CH_2O)$—), 1.51-1.12 (m, 21H, SH+—$CH_2$—+$H_{Cyclo}$).

Compound L5: $^1H$ NMR (400 MHz, $CDCl_3$, TMS): δ 8.37 (d, 1H, $H_{Ar}$), 7.98 (d, 1H, $H_{Ar}$), 7.69-7.61 (m, 3H, $H_{Ar}$), 7.59-7.48 (m, 1H, $H_{Ar}$), 4.38 (br, 2H, —$NCH_2$—Ar), 3.76 (br, 2H, —$CH_2O$—) 3.72-3.62 (m, 14H, —$CH_2O$—+—$OCH_2$—($CH_2N$)—), 3.61-3.55 (m, 2H, —$CH_2N$—), 3.23 (s, 6H, —($CH_3)_2N$—), 3.07 (s, 3H, —$CH_3SO^-_3$—), 2.52 (q, 2H, —$CH_2S$—), 1.67-1.51 (m, 4H, —($SCH_2$)$CH_2$+—$CH_2(CH_2O)$—), 1.35-1.21 (m, 15H, —SH+—$CH_2$—).

Compound L6: $^1H$ NMR (400 MHz, $CDCl_3$, TMS): δ 3.94 (br, 2H, —$CH_2O$—), 3.75-3.52 (m, 16H, —$CH_2O$—+—$OCH_2$—($CH_2N$)—+—$CH_2$—OH), 3.48 (t, 2H, —$CH_2N$—), 3.39-3.31 (m, 2H, —$NCH_2$—), 3.25 (s, 6H, —($CH_3)_2N$—), 3.2 (br, 1H, —OH), 2.89 (s, 3H, —$CH_3SO^-_3$—), 2.52 (q, 2H, —CH$_2$S—), 2.35-2.26 (m, 2H, —(NCH$_2$)CH$_2$—), 1.70-1.52 (m, 4H, +(SCH$_2$)CH$_2$+—CH$_2$(CH$_2$O)—), 1.36-1.21 (m, 15H, —SH+—CH$_2$—).

Compound L7: $^1$H NMR (400 MHz, CDCl$_3$, TMS): δ 4.78 (br, 1H, —CHOH(CH2OH)—), 4.59 (br, 1H, —CH2OH—), 4.50-4.45 (m, 1H, —CHOH(CH2OH)—), 4.43 (d and br, 2H, —CH$_2$O—), 3.95 (d and br, 2H, —CH2N—), 3.86-3.76 (d and br, 2H, —CH$_2$—OH), 3.75-3.55 (m, 14H, —CH$_2$O—+—OCH$_2$—(CH$_2$N)—), 3.48 (t, 2H, —NCH$_2$—), 3.34 (s, 6H, —(CH$_3$)$_2$N—), 2.99 (s, 3H, —CH$_3$SO$^-$$_3$—), 2.52 (q, 2H, —CH$_2$S—), 1.71-1.51 (m, 4H, +(SCH$_2$)CH$_2$+—CH$_2$(CH$_2$O)—), 1.42-1.21 (m, 15H, —SH+—CH$_2$—).

Compound L8: $^1$H NMR (400 MHz, CDCl$_3$, TMS): δ 3.96 (br, 2H, —CH$_2$O—), 3.79-3.75 (m, 1H, H$_{Cyclo}$), 3.66-3.57 (m, 14H, —CH$_2$O—+—OCH$_2$—(CH$_2$N)—), 3.46 (t, 2H, —CH$_2$N—), 3.12 (s, 6H, —(CH$_3$)$_2$N—), 2.89 (s, 3H, —CH$_3$SO$^-$$_3$—), 2.52 (q, 2H, —CH$_2$S—), 2.28 (d, 2H, H$_{Cyclo}$), 2.01 (d, 2H, H$_{Cyclo}$), 1.64-1.54 (m, 4H, —(SCH$_2$)CH$_2$+—CH$_2$(CH$_2$O)—), 1.47 (q, 2H, H$_{Cyclo}$), 1.33 (t, $^3$J=8.0 Hz, 1H, —SH), 1.30-1.22 (m, 14H, —CH2-), 1.16 (q, 2H, H$_{Cyclo}$) 1.04 (td, 1H —CHC—), 0.86 (s, 9H, —C(CH$_3$)$_3$—).

Compound L9: $^1$H NMR (400 MHz, CDCl$_3$, TMS): δ 7.82 (d, 2H, H$_{Ar}$), 7.66-7.51 (m, 3H, H$_{Ar}$), 4.24 (br, 2H, —CH$_2$O—), 3.78 (s, 6H, —(CH$_3$)$_2$N—), 3.68-3.52 (m, 14H, —CH$_2$O—+—OCH$_2$—(CH$_2$N)—), 3.47-3.36 (m, 2H, —CH$_2$N—), 2.87 (s, 3H, —CH$_3$SO$^-$$_3$—), 2.52 (q, 2H, —CH$_2$S—), 1.70-1.46 (m, 4H, —(SCH$_2$)CH$_2$+—CH$_2$(CH$_2$O)—), 1.42-1.1.16 (m, 15H, —SH+—CH$_2$—).

Compound L10: $^1$H NMR (400 MHz, CDCl$_3$, TMS): δ 3.98 (br, 2H, —CH$_2$O—), 3.78-3.75 (m, 1H, H$_{Cyclo}$), 3.64-3.55 (m, 14H, —CH$_2$O—+—OCH$_2$—(CH$_2$N)—), 3.46-3.42 (m, 2H, —CH$_2$N—), 3.16 (s, 6H, —(CH$_3$)$_2$N—), 2.86 (s, 3H, —CH$_3$SO$^-$$_3$—), 2.52 (q, 2H, —CH$_2$S—), 1.93-1.40 (m, 26H, SCH$_2$)CH$_2$+—CH(CH$_2$O)—+H$_{Cyclo}$), 1.33 (t, $^3$J=7.82 Hz, 1H, —SH), 1.29-1.24 (m, 14H, —CH$_2$—).

Compound L11: $^1$H NMR (400 MHz, CDCl$_3$, TMS): δ 7.4-7.2 (m, 4H, H$_{Ar}$), 7.17 (d, 1H, H$_{Ar}$), 3.95 (d and br, 2H, —CH$_2$O—), 3.79-3.52 (m, 14H, —CH$_2$O—+—OCH$_2$—(CH$_2$N)—), 3.45 (q, 2H, —CH$_2$N—), 3.29-3.22 (in and br, 1H, H$_{Cyclo}$), 3.01-2.92 (in and br, 1H, H$_{Cyclo}$) 2.87 (s, 3H, —CH$_3$SO$^-$$_3$—), 2.81 (d and br, 6H, —(CH$_3$)$_2$N—), 2.52 (q, 2H, —CH$_2$S—), 2.39-2.26 (m, 2H, H$_{Cyclo}$), 2.19-2.06 (m, 2H, H$_{Cyclo}$), 1.96-1.84 (m, 4H, H$_{Cyclo}$), 1.72-1.53 (m, 4H, —(SCH$_2$)CH$_2$+—CH$_2$(CH$_2$O)—), 1.42-1.1.19 (m, 15H, —SH+—CH$_2$—).

Compound L12: $^1$H NMR (400 MHz, CDCl$_3$, TMS): δ 7.42 (d, 2H, H$_{Ar}$), 7.37-2.27 (m, 8H, H$_{Ar}$), 7.25-7.18 (t, 2H, H$_{Ar}$), 5.13 (s, 1H, H$_{Ar}$), 4.12 (br, 2H, —CH$_2$O—), 3.96 (br, 2H, —NCH$_2$(CH$_2$OCAr), 3.64-3.51 (m, 14H, —CH$_2$O—+—OCH$_2$—(CH$_2$N)—), 3.45 (t, 2H, —CH$_2$N—), 3.29-3.34 (m, 2H, —CH$_2$OCAr—), 3.28 (s, 6H, —(CH$_3$)$_2$N—), 2.86 (s, 3H, —CH$_3$SO$^-$$_3$—), 2.52 (q, 2H, —CH$_2$S—), 1.60-1.48 (m, 4H, —(SCH$_2$)CH$_2$+—CH$_2$(CH$_2$O)—), 1.34-1.16 (m, 15H, —SH+—CH$_2$—).

Compound L13: $^1$H NMR (400 MHz, CDCl$_3$, TMS): δ 3.96 (br, 2H, CH$_2$O—), 3.72 (s, 1H, —(CH$_3$)$_2$NCH—), 3.70-3.53 (m, 14H, —CH$_2$O—+—OCH$_2$—(CH$_2$N)—), 3.46 (t, 2H, —CH$_2$N—), 3.33 (s, 6H, —CH(OCH$_3$)$_2$), 3.28 (s, 6H, —(CH$_3$)$_2$N—), 2.89 (s, 3H, —CH$_3$SO$^-$$_3$—), 2.51 (q, 2H, —CH$_2$S—), 1.69-1.53 (m, 4H, (SCH$_2$)CH$_2$+—CH$_2$(CH$_2$O)—), 1.40-1.23 (m, 15H, —SH+—CH$_2$—+—(NCH$_2$)CH$_3$).

Example 7

Synthesis of Ligand L14

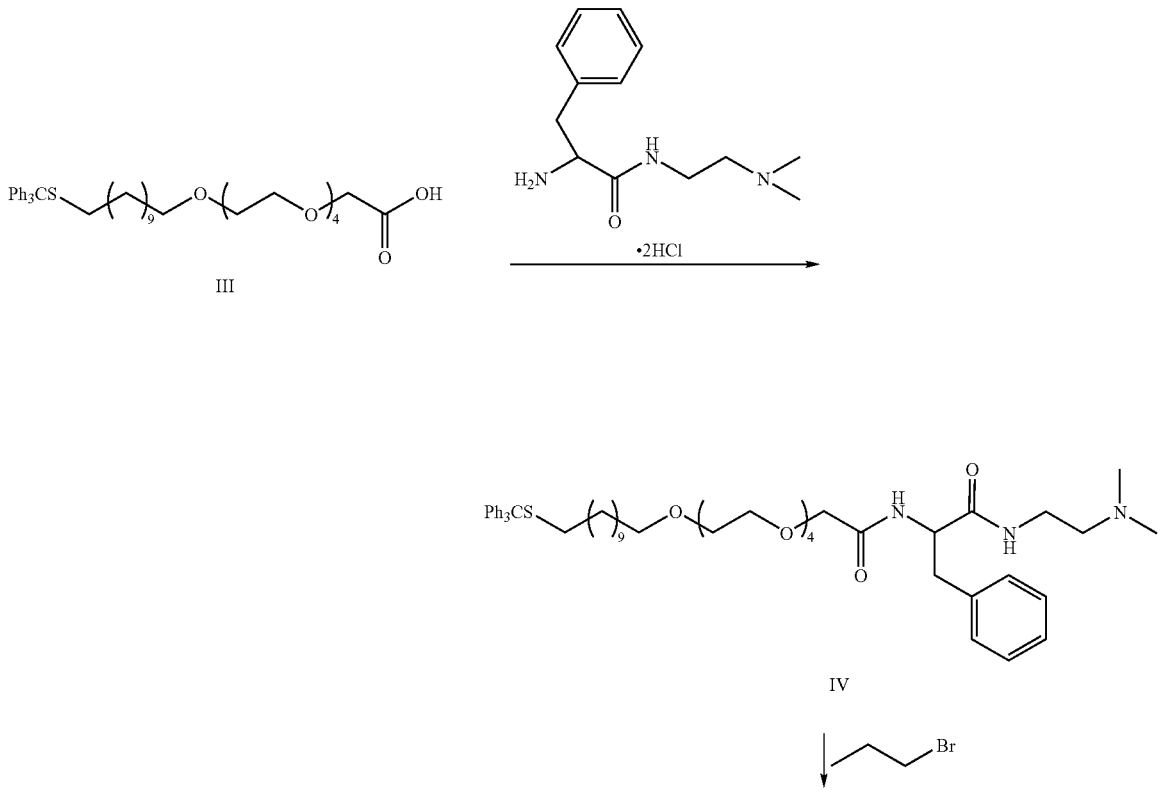

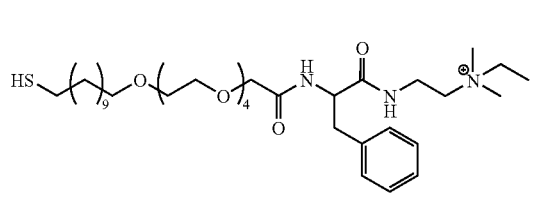

L14

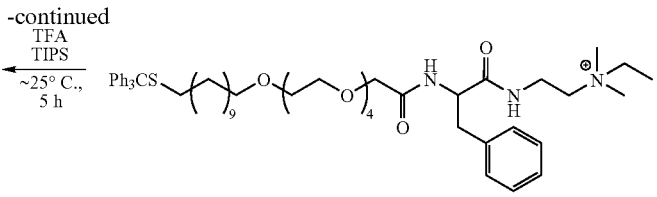

V

Procedure: Compound IV bearing L-Phe group was synthesized through the reaction of 1,1,1-triphenyl-14,17,20,23,26-pentaoxa-2-thiaoctacosan-28-oic acid (III) with corresponding 2-amino-N-(2-(dimethylamino)ethyl)-3-phenylpropanamide. Briefly, compound III was dissolved in a mixture of dry DCM and DMF that was placed in an ice-bath. When the temperature reached about 0° C., corresponding L-phenylaline derivative, 1-ethyl-3-(3-dimethylaminopropyl)carbodiimide (EDC), N-hydroxybenzotriazole (HOBt), and sodium bicarbonate were added. The mixture was stirred at room temperature for 24 h. Subsequently, the solution was poured into water and extracted with ethyl acetate (EtOAc). The organic layers were combined and washed successively with saturated sodium bicarbonate and brine. After drying over sodium sulfate, the solvent was removed under reduced pressure. The residue was charged on $SiO_2$ column for purification. EtOAc/MeOH (90:10) and EtOAc/MeOH/$NH_4OH$ (90:10:1) were used as gradient eluent. Compound V was obtained through nucleophilic substitution of compound IV with bromoethane. The trityl protected thiol ligand (V) was dissolved in dry DCM. TFA and TIPS were added successively. The reaction mixture was stirred at room temperature for ~5 h. Subsequently, the solvent was removed under reduced pressure. The residue was washed thoroughly with diethyl ether to remove the residual TFA and TIPS. After drying in high vacuum, the product L14 (5-benzyl-N-ethyl-32-mercapto-N,N-dimethyl-4,7-dioxo-9,12,15,18,21-pentaoxa-3,6-diazadotriacontan-1-aminium) was obtained in quantitative yield. Its structure was confirmed by $^1H$ NMR.

Compound L14: $^1H$ NMR (400 MHz, $CDCl_3$, TMS): δ 8.48 (br t, 1H, —NH—), 7.65 (br d, 1H, —NH—), 7.25 (m, 5H, $H_{Ar}$), 4.61 (m, 1H, —CH<), 4.03 (q, 2H, —$OCH_2$—), 3.8~3.4 (m, 22H, —$OCH_2$—+—$CH_2$—), 3.14 (m, 2H, —$CH_2$Ar), 3.11 (s, 6H, —$CH_3$), 2.90 (m, 2H, —$CH_2$—), 2.52 (q, 2H, —$SCH_2$—), 1.58 (m, 4H, —$CH_2$—), 1.26 (m, 17H, —$CH_2$—+—$CH_3$).

Example 8

Fabrication of Cationic Gold Nanoparticles

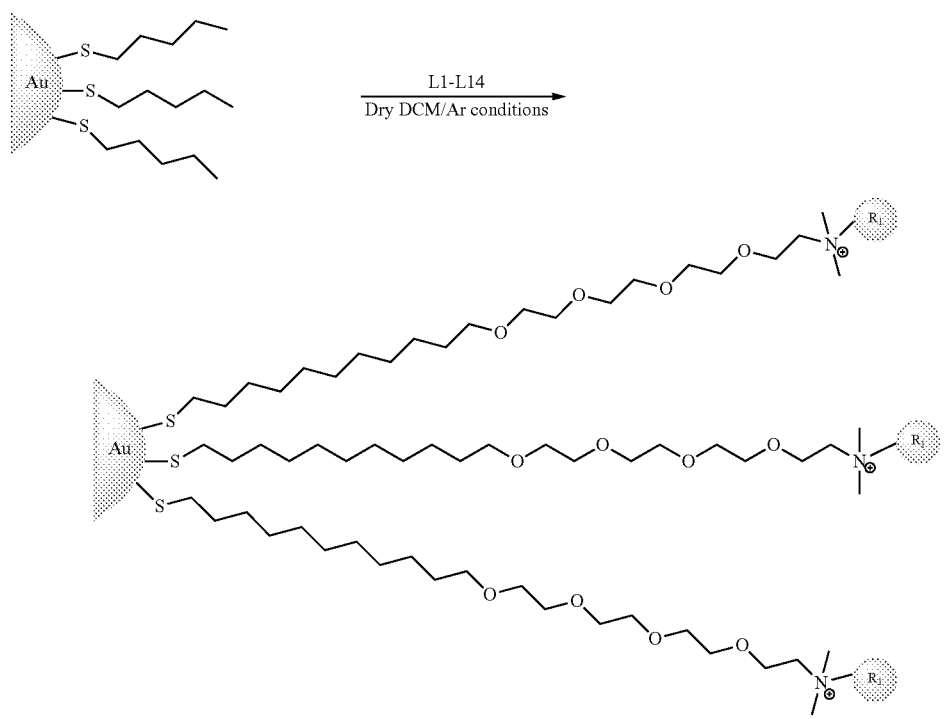

-continued

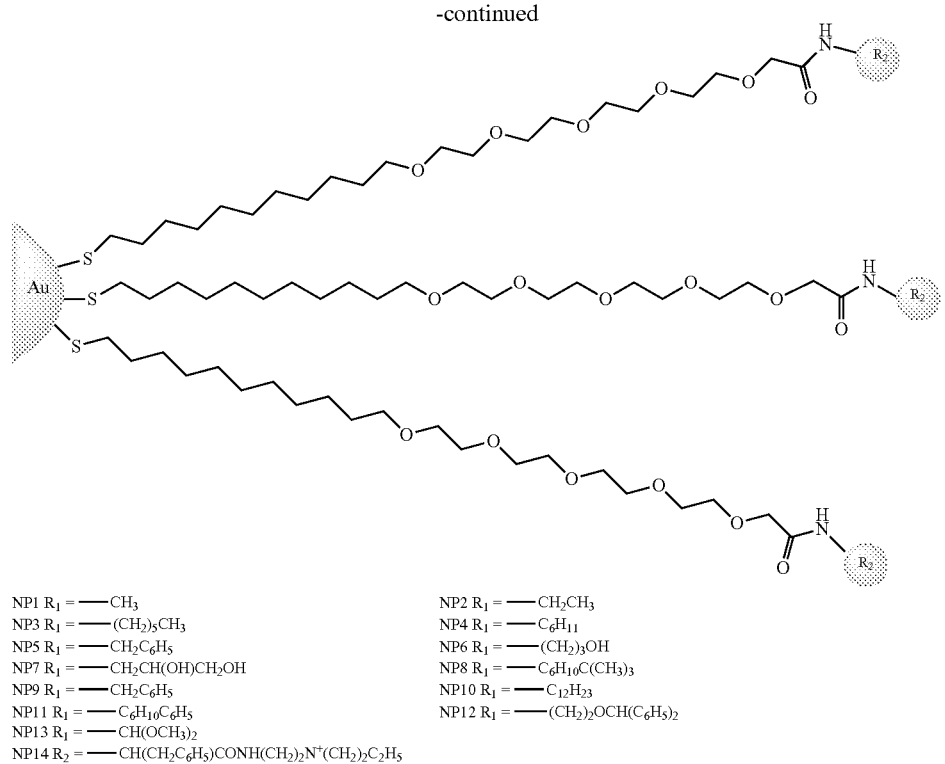

NP1 R₁ = —CH₃
NP3 R₁ = —(CH₂)₅CH₃
NP5 R₁ = —CH₂C₆H₅
NP7 R₁ = —CH₂CH(OH)CH₂OH
NP9 R₁ = —CH₂C₆H₅
NP11 R₁ = —C₆H₁₀C₆H₅
NP13 R₁ = —CH(OCH₃)₂
NP14 R₂ = —CH(CH₂C₆H₅)CONH(CH₂)₂N⁺(CH₂)₂C₂H₅

NP2 R₁ = —CH₂CH₃
NP4 R₁ = —C₆H₁₁
NP6 R₁ = —(CH₂)₃OH
NP8 R₁ = —C₆H₁₀C(CH₃)₃
NP10 R₁ = —C₁₂H₂₃
NP12 R₁ = —(CH₂)₂OCH(C₆H₅)₂

General procedure: 1-Pentanethiol coated gold nanoparticles (d=~2 nm) were prepared according to a previously reported protocol. (Brost, et al., *J. Chem. Soc. Chem. Commun.*, 1994, 801.) Place-exchange reaction of compound Ls dissolved in DCM with pentanethiol-coated gold nanoparticles (d~2 nm) was carried out for 3 days at ambient temperature. (See, Hostetler, et al., *Langmuir*, 1999, 15, 3782.) Then, DCM was evaporated under reduced pressure. The residue was dissolved in a small amount of distilled water and dialyzed (membrane MWCO=1,000) to remove excess ligands, acetic acid and the other salts present with the nanoparticles. After dialysis, the particles were lyophilized to afford a brownish solid. The nanoparticles are redispersed in deionized water (18 MΩ-cm). $^1$H NMR spectra in D₂O showed substantial broadening of the proton signals and no free ligands were observed.

Example 9

Fluorescence Titration

In the fluorescent titration experiment between nanoparticles and GFP, the change of fluorescence intensity at 510 nm was measured with an excitation wavelength of 475 nm at various concentrations of nanoparticles from 0 to 100 nM on a Molecular Devices SpectaMax M5 microplate reader at 25° C. The decrease of fluorescent intensity of 100 nM GFP was observed with increase of nanoparticle concentration. Non-linear least-squares curve-fitting analysis was done to estimate the binding constant (Ks) and association stoichiometry (n) using the model in which the nanoparticle is assumed to possess n equivalent of independent binding sites.

TABLE 3

Binding constants ($K_s$), Gibbs free energy changes ($-\Delta G$) and binding stoichiometries (n) between GFP and cationic nanoparticles (NP1-NP14) as determined from fluorescence titration.

| Nanoparticle | $K_s$ ($10^9$ M$^{-1}$) | $-\Delta G$ (kJ mol$^{-1}$) | n |
|---|---|---|---|
| NP1 | 22.7 | 59.1 | 3.9 |
| NP2 | 2.6 | 53.7 | 2.8 |
| NP3 | 51.3 | 61.1 | 2.2 |
| NP4 | 15.9 | 58.2 | 3.6 |
| NP5 | 30.7 | 59.9 | 4.1 |
| NP6 | 9.4 | 56.9 | 1.8 |
| NP7 | 0.5 | 49.7 | 4.7 |
| NP8 | 1.1 | 51.6 | 7.9 |
| NP9 | 0.2 | 47.4 | 3.3 |
| NP10 | 0.5 | 49.7 | 9.7 |
| NP11 | 9.3 | 56.9 | 4.4 |
| NP12 | 83.9 | 62.3 | 3.3 |
| NP13 | 0.1 | 45.7 | 6.2 |
| NP14 | 0.2 | 47.4 | 1.6 |

Example 10

Training Matrix of Fluorescence Response Patterns

To create the training matrix GFP and nanoparticles were mixed stoichiometrically (in the ratio obtained from fluorescent titration, Table 3). After incubation for 15 min 200 μL of each solution was respectively loaded into a well on a 96-well plate (300 μL Whatman black bottom microplate) and the fluorescent intensity at 510 nm was recorded on a Molecular Devices SpectraMax M5 microplate reader with excitation at 490 nm. Subsequently, 10 μL of protein solution of two different concentrations with defined absorbance value at 280 nm was added and incubated for 30 min. the fluorescence intensity at 510 nm was recorded again. The difference between the two intensities before and after addition of proteins was considered as the fluorescent response (Table 4-5).

TABLE 4

Training matrix of fluorescence response patterns of NP-GFP sensor array (NP1-NP14) against various proteins with identical absorption values of A = 0.005 at 280 nm.

| Protein | NP1 | NP2 | NP3 | NP4 | NP5 | NP6 | NP7 | NP8 | NP9 | NP10 | NP11 | NP12 | NP13 | NP14 |
|---|---|---|---|---|---|---|---|---|---|---|---|---|---|---|
| BSA | 305.947 | 586.768 | 619.605 | 620.25 | 482.418 | 426.364 | 496.553 | 131.036 | 183.982 | 10.452 | 208.106 | 176.631 | 83.047 | −46.55 |
| BSA | 316.748 | 636.133 | 668.244 | 494.015 | 511.874 | 440.594 | 547.516 | 169.5 | 221.068 | 30.619 | 270.807 | 224.564 | 137.383 | 218.135 |
| BSA | 333.064 | 594.562 | 680.864 | 650.388 | 577.526 | 522.811 | 558.175 | 179.789 | 227.657 | 83.085 | 226.618 | 232.581 | 206.579 | 253.711 |
| BSA | 326.327 | 652.608 | 676.664 | 642.604 | 511.681 | 506.838 | 550.274 | 203.991 | 252.626 | 76.01 | 330.791 | 266.989 | 199.624 | 254.06 |
| BSA | 363.045 | 636.766 | 659.335 | 603.398 | 519.898 | 449.822 | 544.564 | 182.464 | 26.636 | 100.337 | 228.191 | 276.871 | 155.28 | 263.51 |
| BSA | 396.199 | 616.517 | 369.392 | 638.444 | 514.032 | 486.928 | 554.403 | 162.855 | 185.218 | 44.299 | 234.272 | 234.931 | 181.22 | 269.804 |
| PhosA | −33.506 | 500.536 | 546.989 | 292.497 | 176.586 | 488.444 | 191.854 | −1.19 | 389.137 | 10.53 | 94.891 | 49.975 | 40.62 | 416.115 |
| PhosA | −23.249 | 539.312 | 530.609 | 256.467 | 164.017 | 435.963 | 143.927 | −1.265 | 344.785 | 13.606 | 94.398 | 52.274 | 38.112 | 422.53 |
| PhosA | −47.58 | 496.14 | 565.61 | 243.709 | 204.957 | 495.996 | 188.762 | −3.082 | 283.612 | 13.848 | 87.009 | 60.852 | 34.103 | 449.05 |
| PhosA | −41.923 | 452.131 | 578.209 | 317.626 | 190.385 | 457.067 | 198.34 | −8.381 | 279.713 | 19.313 | 121.156 | 63.63 | 36.276 | 433.001 |
| PhosA | −50.614 | 531.205 | 586.317 | 272.643 | 220.909 | 481.873 | 185.018 | −15.514 | 289.573 | 13.727 | 107.27 | 87.497 | 36.037 | 444.906 |
| PhosA | −40.317 | 489.328 | 531.233 | 245.404 | 306.373 | 499.276 | 194.883 | −9.516 | 284.757 | −1.272 | 90.733 | 48.788 | 39.653 | 436.602 |
| α-Am | −61.599 | 67.852 | 64.489 | 29.399 | 27.583 | 35.276 | −52.981 | −19.245 | 156.276 | −9.485 | 15.168 | 42.442 | 10.998 | 65.816 |
| α-Am | −66.192 | 56.444 | 85.053 | 45.143 | 13.538 | 73.54 | −30.928 | −20.458 | 226.818 | −2.206 | 12.314 | 31.208 | 17.156 | 34.442 |
| α-Am | −64.418 | 53 | 115.641 | 23.581 | 31.327 | 56.196 | −22.054 | 14.207 | 200.874 | −0.106 | 11.45 | 71.179 | 15.163 | 35.489 |
| α-Am | −65.412 | 43.465 | 78.981 | 23.057 | 26.825 | 52.771 | −32.981 | −16.046 | 270.027 | 1.265 | 13.669 | 52.224 | 19.774 | 42.835 |
| α-Am | −68.39 | 58.072 | 113.644 | 30.656 | 16.54 | 26.787 | −20.938 | −9.959 | 169.345 | 9.203 | 14.511 | 32.234 | 12.674 | 48.692 |
| α-Am | −74.054 | 71.985 | 87.721 | 37.474 | 26.702 | 60.815 | −28 | −9.362 | 210.004 | 2.645 | 11.164 | 60.213 | 36.862 | 86.14 |
| Lip | 352.799 | 601.55 | 567.522 | 735.012 | 776.911 | 574.878 | 556.279 | 582.261 | 702.076 | 518.092 | 754.973 | 249.488 | 530.161 | 361.55 |
| Lip | 361.736 | 621.07 | 572.772 | 744.669 | 748.464 | 580.221 | 569.223 | 659.26 | 736.293 | 592.369 | 797.132 | 277.894 | 502.916 | 337.622 |
| Lip | 302.231 | 612.397 | 627.57 | 757.208 | 698.016 | 587.677 | 567.56 | 594.791 | 805.38 | 605.932 | 811.525 | 305.1 | 465.534 | 340.243 |
| Lip | 370.342 | 589.636 | 544.18 | 747.731 | 721.71 | 487.906 | 556.098 | 596.099 | 715.959 | 614.634 | 802.534 | 276.853 | 509.879 | 351.938 |
| Lip | 343.718 | 597.248 | 623.797 | 739.92 | 731.703 | 576.65 | 571.673 | 547.211 | 779.571 | 560.616 | 829.155 | 264.174 | 460.299 | 355.821 |
| Lip | 306.718 | 588.043 | 589.907 | 740.567 | 723.991 | 619.14 | 577.672 | 557.785 | 789.359 | 528.403 | 822.188 | 258.561 | 449.646 | 326.933 |
| β-gal | −89.286 | 198.872 | 399.406 | 257.162 | 205.085 | 274.188 | 38.232 | 44.632 | 455.431 | 36.93 | 245.896 | 125.039 | 18.336 | 182.777 |
| β-gal | −94.609 | 204.162 | 390.307 | 225.941 | 234.471 | 271.992 | 14.624 | 49.594 | 436.36 | 36.274 | 239.73 | 135.282 | 25.392 | 185.33 |
| β-gal | −97.575 | 227.428 | 381.902 | 211.245 | 197.649 | 228.467 | 21.64 | 62.673 | 419.01 | 31.219 | 256.196 | 154.625 | 21.917 | 128.503 |
| β-gal | −98.533 | 243.865 | 394.869 | 233.13 | 197.359 | 238.018 | 40.411 | 48.363 | 445.806 | 37.945 | 238.561 | 135.003 | 31.63 | 136.625 |
| β-gal | −119.27 | 208.595 | 376.448 | 247.481 | 209.845 | 238.538 | 24.004 | 46.481 | 456.508 | 36.191 | 260.665 | 137.536 | 22.817 | 194.155 |
| β-gal | −93.272 | 205.207 | 410.639 | 246.612 | 197.032 | 285.152 | 43.9 | 40.737 | 426.849 | 33.025 | 272.751 | 114.969 | 19.365 | 173.599 |
| SubA | −66.693 | −90.756 | −64.45 | −15.199 | 5.083 | −111.58 | −95.643 | −7.032 | −14.03 | −6.541 | 9.449 | 1.331 | −4.69 | −113.13 |
| SubA | −74.97 | −85.61 | −79.832 | −21.62 | 2.721 | −126.39 | −112.09 | −5.444 | −18.555 | −5.574 | 2.142 | −8.709 | −9.341 | −132.85 |
| SubA | −63.211 | −86.316 | −84.441 | −23.411 | 10.372 | −137.03 | −113.08 | −1.997 | −14.248 | −4.836 | 8.495 | −16.608 | −7.12 | −137.80 |
| SubA | −73.375 | −89.251 | −79.02 | −21.815 | 1.96 | −133.91 | −110.80 | −3.259 | −16.146 | −3.97 | 3.779 | −18.344 | −9.141 | −126.07 |
| SubA | −83.183 | −102.29 | −79.175 | −21.106 | 5.033 | −138.92 | −115.22 | −2.962 | −17.048 | 0.067 | 2.679 | −12.786 | −9.926 | −136.63 |
| SubA | −75.098 | −96.688 | −82.102 | −8.787 | 2.82 | −129.17 | −118.64 | 1.265 | −13.61 | 2.056 | 3.637 | −13.175 | −9.809 | −139.40 |
| Hem | −139.35 | −7.676 | 92.118 | 48.354 | 18.12 | −54.413 | −50.596 | −4.408 | 144.359 | 19.507 | 65.858 | 163.024 | 12.987 | −10.18 |
| Hem | −118.74 | −8.143 | 96.509 | 18.004 | 16.347 | −41.365 | −51.108 | −3.759 | 139.012 | 30.239 | 66.148 | 165.159 | 7.949 | 4.575 |
| Hem | −116.67 | 9.571 | 111.381 | 21.724 | 16.551 | −65.757 | −41.59 | 0.006 | 132.334 | 13.48 | 69.558 | 161.399 | 11.924 | −9.867 |
| Hem | −111.19 | 2.4 | 153.414 | 31.365 | 19.865 | −58.723 | −32.973 | −1.448 | 139.794 | 21.403 | 62.875 | 166.952 | 8.05 | 17.018 |
| Hem | −116.58 | 20.933 | 111.707 | 27.528 | 17.863 | −66.483 | −41.76 | −6.173 | 144.44 | 17.299 | 66.135 | 178.887 | 5.495 | −2.983 |
| Hem | −129.45 | 28.529 | 118.086 | 32.863 | 26.705 | −51.502 | −32.023 | −0.027 | 148.115 | 12.603 | 74.179 | 170.022 | 18.203 | 10.792 |
| His | 1.78 | 33.633 | 45.467 | 35.289 | 23.814 | 41.634 | 10.517 | 0.703 | 33.805 | 9.046 | 23.694 | 25.012 | 27.773 | 4.377 |
| His | −5.621 | 24.594 | 44.68 | 32.208 | 22.176 | 38.057 | 14.094 | 3.034 | 33.182 | 11.698 | 22.75 | 22.67 | 34.236 | 5.077 |
| His | 0.199 | 25.129 | 46.877 | 41.282 | 23.15 | 37.655 | 6.069 | 4.253 | 32.42 | 14.315 | 21.097 | 22.477 | 27.955 | 5.9 |
| His | −2.705 | 24.978 | 47.117 | 34.57 | 21.145 | 36.45 | 7.688 | 2.378 | 30.756 | 12.815 | 20.843 | 4.927 | 28.679 | 5.905 |
| His | 12.668 | 30.173 | 47.039 | 33.019 | 23.26 | 31.6 | 8.392 | 1.244 | 29.38 | 14.528 | 18.834 | 19.799 | 31.393 | 5.833 |
| His | −4.724 | 30.959 | 45.794 | 30.751 | 23.329 | 37.471 | 12.561 | 7.275 | 30.888 | 14.148 | 18.254 | 6.6 | 23.024 | 13.615 |
| HSA | 197.813 | 403.073 | 545.966 | 509.668 | 271.053 | 311.58 | 333.308 | 261.715 | 574.438 | 283.847 | 236.676 | 430.715 | 239.041 | 56.606 |
| HSA | 228.466 | 445.963 | 586.049 | 565.702 | 434.639 | 360.935 | 342.007 | 281.958 | 602.046 | 292.186 | 394.182 | 446.809 | 255.308 | 81.061 |
| HSA | 263.722 | 455.332 | 584.686 | 574.706 | 421.475 | 383.949 | 382.193 | 295.873 | 627.377 | 304.411 | 400.131 | 461.193 | 255.084 | 89.714 |
| HSA | 254.063 | 475.59 | 559.118 | 581.031 | 439.124 | 347.986 | 379.654 | 291.802 | 591.651 | 307.127 | 408.517 | 458.672 | 254.945 | 98.359 |
| HSA | 262.169 | 461.449 | 558.482 | 564.128 | 462.037 | 382.175 | 388.159 | 294.29 | 615.643 | 309.649 | 399.744 | 476.204 | 249.319 | 92.153 |
| HSA | 248.059 | 464.747 | 556.678 | 558.715 | 452.979 | 361.971 | 379.654 | 293.318 | 608.757 | 314.08 | 413.308 | 470.652 | 257.587 | 100.494 |
| PhosB | 101.717 | 554.461 | 653.802 | 683.579 | 617.953 | 471.019 | 397.716 | 384.647 | 719.31 | 257.697 | 731.094 | 270.731 | 254.668 | 301.571 |
| PhosB | 106.995 | 564.017 | 663.209 | 726.067 | 631.624 | 484.963 | 344.2 | 391.537 | 748.024 | 286.668 | 736.699 | 292.243 | 253.271 | 317.912 |
| PhosB | 118.486 | 611.545 | 682.132 | 734.942 | 563.922 | 468.789 | 400.585 | 390.982 | 717.193 | 275.217 | 766.183 | 306.711 | 260.862 | 366.691 |
| PhosB | 83.929 | 536.322 | 711.86 | 717.314 | 624.441 | 483.712 | 353.169 | 397.648 | 761.517 | 274.707 | 764.668 | 301.862 | 259.233 | 302.474 |
| PhosB | 88.855 | 579.743 | 697.315 | 598.581 | 627.713 | 468.756 | 355.403 | 400.259 | 736.147 | 268.324 | 750.177 | 319.835 | 251.146 | 337.906 |
| PhosB | 96.071 | 548.849 | 680.108 | 729.603 | 600.591 | 483.159 | 381.61 | 492.097 | 737.988 | 278.856 | 740.982 | 352.473 | 272.823 | 334.238 |
| Myo | −51.732 | −36.418 | −9.821 | −0.645 | −2.495 | −59.007 | −60.728 | −18.779 | 6.184 | −2.003 | 14.803 | 33.859 | −5.431 | −73.326 |
| Myo | −48.981 | −45.299 | −21.132 | −3.737 | 54.227 | −88.059 | −71.349 | −12.934 | 2.528 | −10.342 | 9.31 | 36.423 | −7.387 | −78.783 |
| Myo | −66.146 | −45.166 | −15.578 | 18.27 | 9.218 | −70.705 | −63.198 | −11.36 | 0.5 | 0.306 | 10.344 | 41.896 | −5.66 | −104.44 |
| Myo | −89.125 | −46.242 | −9.75 | 15.357 | 10.392 | −36.185 | −64.84 | −8.471 | 0.024 | −6.234 | 11.507 | 38.878 | 12.779 | −67.097 |
| Myo | −64.406 | −43.56 | −17.185 | −1.351 | 1.281 | −76.184 | −67.625 | −9.872 | 2.624 | −1.145 | 8.321 | 49.628 | −7.035 | −66.604 |
| Myo | −47.776 | −31.758 | −20.121 | −7.002 | 2.296 | −62.981 | −68.097 | −0.263 | 5.207 | −10.763 | 12.808 | 32.987 | −6.466 | −53.89 |

TABLE 5

Training matrix of fluorescence response patterns of NP-GFP sensor array (NP1-NP14) against various proteins with identical absorption values of A = 0.0005 at 280 nm.

| Protein | NP1 | NP2 | NP3 | NP4 | NP5 | NP6 | NP7 | NP8 | NP9 | NP10 | NP11 | NP12 | NP13 | NP14 |
|---|---|---|---|---|---|---|---|---|---|---|---|---|---|---|
| BSA | −72.214 | 22.546 | 66.218 | 8.275 | 14.504 | 269.754 | −28.161 | −0.119 | 3.027 | 18.652 | 2.271 | 14.828 | 11.981 | 93.014 |
| BSA | −73.592 | 19.65 | 67.859 | 15.445 | 15.87 | −9.161 | −55.822 | 5.569 | 11.739 | −8.183 | 6.841 | 15.73 | 15.698 | 79.086 |
| BSA | −72.607 | 9.662 | 73.834 | 15.255 | 9.883 | −15.974 | −48.594 | −0.486 | −12.615 | 17.186 | 9.531 | −2.083 | 12.669 | 112.855 |
| BSA | −63.455 | 16.383 | 81.674 | 14.517 | 19.712 | −24.671 | −50.037 | 1.726 | 23.45 | −3.831 | 6.732 | −0.533 | 25.111 | 111.408 |
| BSA | −74.029 | −4.492 | 7.00 | 12.657 | 16.91 | 15.023 | −48.623 | 13.951 | 101.375 | −18.63 | 4.639 | 9 | 16.84 | 129.776 |
| BSA | −58.731 | 9.898 | 67.734 | 13.52 | 338.237 | 62.694 | −41.814 | 23.309 | 14.693 | 10.242 | 27.113 | 16.227 | 17.736 | 112.76 |
| PhosA | −40.558 | 22.514 | 73.244 | 4.667 | 11.731 | −2.084 | −13.791 | −10.61 | 5.351 | −23.42 | 9.862 | −12.29 | −1.35 | −26.874 |
| PhosA | −43.66 | 29.401 | 68.935 | 9.457 | 12.924 | 9.449 | −17.706 | −3.576 | 2.056 | −13.18 | 0.162 | 0.126 | −1.6 | −32.203 |
| PhosA | −41.469 | 16.318 | 51.049 | 3.823 | 8.312 | 2.263 | 15.225 | −13.77 | 4.546 | 10.442 | 9.111 | −22.80 | −2.162 | −18.65 |
| PhosA | −43.818 | 33.361 | 52.065 | 8.754 | 9.39 | −3.65 | −30.136 | 1.417 | 2.136 | −19.93 | 3.383 | −6.217 | −0.844 | −13.842 |
| PhosA | −43.624 | 26.951 | 77.328 | 8.299 | 8.559 | −2.801 | −9.23 | −24.18 | 5.771 | 3.371 | 19.339 | −7.592 | 3.497 | −17.416 |
| PhosA | −46.249 | 45.62 | 80.277 | 10.772 | 1.967 | 11.676 | −5.935 | −19.36 | 17.359 | 2.003 | 11.919 | −1.218 | 5.757 | 51.587 |
| α-Am | −42.272 | −13.37 | 2.682 | 8.922 | 9.565 | −88.301 | −38.385 | 11.172 | −3.587 | 1.665 | 5.313 | −20.45 | 0.318 | −101.55 |
| α-Am | −40.581 | −13.95 | −2.339 | 8.6 | 6.3 | −99.757 | −46.264 | −11.81 | −5.289 | −4.388 | 0.465 | −29.08 | 14.326 | −105.98 |
| α-Am | −41.696 | −25.31 | −3.973 | 4.083 | 7.828 | −87.774 | −40.766 | 10.763 | −11.213 | −23.37 | 2.033 | −19.48 | −4.182 | −107.05 |
| α-Am | −39.418 | 3.397 | 0.96 | 5.634 | 6.968 | −90.798 | −48.061 | −0.12 | −8.498 | −9.466 | −0.593 | −36.02 | 2.997 | −115.29 |
| α-Am | −39.457 | −13.35 | −3.875 | −0.558 | 4.612 | −86.642 | −56.215 | 17.163 | −0.06 | 0.673 | −0.135 | −21.47 | −8.306 | −77.366 |
| α-Am | −49.759 | −13.96 | −4.912 | 3.739 | 1.046 | −91.921 | −39.467 | 7.738 | −5.526 | 1.213 | 1.827 | −14.47 | 8.703 | −98.263 |
| Lip | −96.001 | 57.381 | 61.636 | 28.955 | 14.115 | 67.546 | −44.257 | −11.52 | 55.793 | 11.33 | 31.812 | −3.937 | 22.471 | 66.879 |
| Lip | −94.966 | 55.816 | 75.428 | 43.067 | 14.418 | 73.715 | −21.636 | −11.25 | 57.555 | 5.048 | 39.731 | −9.889 | 18.618 | 64.135 |
| Lip | −96.455 | 63.177 | 74.823 | 28.807 | 15.718 | 81.123 | −38.653 | −10.05 | 57.63 | 4.714 | 40.674 | −8.206 | 21.211 | 91.852 |
| Lip | −97.166 | 44.857 | 67.139 | 27.723 | 13.731 | 96.308 | −41.335 | −17.72 | 57.015 | 3.38 | 40.452 | −4.426 | 22.215 | 73.135 |
| Lip | −91.744 | 54.953 | 73.902 | 26.02 | 16.924 | 82.119 | −50.041 | −7.353 | 68.094 | 7.639 | 38.398 | −27.26 | 21.217 | 63.046 |
| Lip | −99.48 | 41.331 | 69.304 | 23.207 | 8.619 | 87.326 | −42.327 | −11.06 | 65.982 | 10.371 | 44.869 | −15.42 | 24.281 | 82.972 |
| β-gal | −95.34 | −68.40 | −20.143 | −12.10 | −2.182 | −58.694 | −113.46 | 0.404 | 9.863 | 4.441 | 10.765 | −9.59 | −11.73 | −46.284 |
| β-gal | −99.627 | −68.97 | −23.807 | −12.85 | −2.614 | 184.778 | −119.04 | −4.809 | 16.47 | −5.125 | 10.506 | −15.59 | −11.15 | −51.669 |
| β-gal | −103.06 | −60.74 | −30.798 | −13.26 | −2.333 | −66.455 | −115.90 | −4.66 | 26.467 | −2.244 | 14.571 | −5.532 | −12.01 | −7.135 |
| β-gal | −98.969 | −39.85 | −31.354 | −17.53 | −1.688 | −51.468 | −121.32 | −7.553 | 309.551 | 22.324 | 135.558 | 13.855 | −6.655 | 156.394 |
| β-gal | −94.742 | −67.2 | −31.958 | −16.65 | −1.309 | −70.196 | −112.68 | −1.704 | 458.419 | 6.213 | 67.506 | 36.616 | 11.68 | 167.393 |
| β-gal | −101.08 | −70.68 | −26.963 | −14.48 | −3.344 | −58.916 | −107.91 | 1.844 | 21.546 | 3.554 | 14.618 | −1.291 | −8.436 | −18.786 |
| SubA | −79.2 | −70.36 | −59.414 | −12.64 | 5.869 | −117.24 | −105.28 | −12.71 | −9.16 | −1.821 | 12.355 | −8.384 | −1.809 | −116.08 |
| SubA | −77.296 | −74.99 | −55.005 | −7.41 | 2.229 | −108.38 | −108.26 | −7.322 | −10.282 | −3.965 | 9.619 | −1.695 | −2.246 | −105.90 |
| SubA | −81.519 | −78.47 | −63.786 | −15.15 | 6.45 | −120.62 | −107.53 | −12.96 | −11.211 | −4.261 | 10.971 | −0.813 | −2.646 | −102.97 |
| SubA | −72.429 | −73.16 | −66.988 | −17.71 | 0.742 | −117.69 | −111.75 | −3.713 | −12.969 | −9.484 | 10.05 | −9.238 | −2.723 | −101.76 |
| SubA | −83.279 | −70.96 | −67.666 | −21.72 | 5.035 | −111.23 | −99.723 | −18.16 | −11.049 | −2.758 | 10.848 | −12.28 | −2.089 | −107.12 |
| SubA | −78.578 | −15.66 | −61.599 | −15.28 | −0.769 | −93.592 | −87.377 | −1.242 | −8.955 | −23.49 | 3.601 | −11.69 | −95.74 | −92.15 |
| Hem | −79.731 | −44.90 | −67.66 | −10.44 | 3.073 | −124.81 | −106.48 | −10.79 | 1.185 | −0.038 | 4.757 | −7.969 | −12.76 | −91.666 |
| Hem | −93.21 | −41.77 | −59.282 | −14.28 | 0.496 | −121.77 | −98.901 | −8.078 | 0.208 | −5.909 | 4.54 | −18.68 | −11.89 | −110.42 |
| Hem | −74.962 | −40.94 | −53.718 | −13.74 | 3.389 | −122.23 | −101.37 | −5.77 | 7.494 | −8.281 | 4.249 | −9.548 | −11.85 | −89.07 |
| Hem | −90.475 | −49.79 | −50.124 | −15.52 | 4.738 | −119.65 | −104.91 | −13.49 | 8.03 | −6.995 | 4.588 | −2.325 | −11.89 | −54.814 |
| Hem | −79.531 | −46.95 | −50.017 | −12.15 | 7.38 | −112.76 | −95.734 | −8.798 | 7.009 | 6.287 | 5.246 | −11.22 | −12.99 | −75.238 |
| Hem | −67.037 | −47.60 | −60.524 | −12.58 | 1.808 | −118.66 | −102.58 | −4.539 | 7.799 | −3.614 | 5.487 | −16.44 | −10.61 | −76.436 |
| His | −18.514 | −22.10 | 1.069 | 3.697 | 6.945 | −14.516 | −22.096 | −1.835 | 3.95 | 8.407 | 4.975 | −7.898 | 0.945 | −38.055 |
| His | −19.325 | −19.35 | 2.001 | 5.298 | 5.089 | −15.718 | −23.027 | −1.65 | 2.96 | 2.819 | 3.64 | −9.339 | 1.797 | −36.346 |
| His | −19.326 | −22.21 | 1.635 | 3.527 | 8.398 | −15.195 | −23.851 | 1.71 | 2.721 | 1.108 | 3.469 | −7.421 | 1.216 | −36.313 |
| His | −17.67 | −19.65 | 1.73 | 3.368 | 4.74 | −15.053 | −27.065 | 0.525 | 2.292 | 3.025 | 3.965 | −9.847 | 0.141 | −36.06 |
| His | −17.892 | −25.61 | 0.326 | 2.076 | 6.189 | −15.52 | −21.965 | −2.726 | 2.157 | 10.829 | 2.754 | −5.678 | 0.342 | −44.226 |
| His | −20.719 | −23.26 | 0.092 | 1.361 | 0.934 | −16.197 | −22.068 | −2.802 | 2.867 | 6.448 | 0.98 | −6.028 | 1.24 | −41.11 |
| HSA | −133.07 | 73.294 | 200.114 | 46.446 | 63.741 | 164.916 | −59.509 | −2.617 | 82.961 | 2.399 | 69.908 | 57.576 | 11.529 | 87.763 |
| HSA | −130.59 | 57.99 | 178.574 | 37.794 | 41.89 | 148.54 | −56.392 | −8.952 | 81.27 | 3.496 | 59.704 | 50.513 | 12.318 | 67.627 |
| HSA | −132.86 | 55.496 | 142.899 | 43.78 | 26.818 | 152.076 | −61.279 | −5.206 | 95.357 | 2.278 | 71.314 | 54.891 | 10.577 | 90.567 |
| HSA | −132.25 | 46.17 | 166.017 | 42.584 | 26.207 | 154.675 | −70.441 | −4.918 | 83.837 | −0.64 | 74.933 | 55.326 | 10.673 | 93.711 |
| HSA | −104.06 | 32.107 | 148.306 | 42.792 | 25.873 | 128.401 | −41.496 | −1.93 | 84.638 | 2.077 | 79.765 | 56.567 | 13.016 | 76.048 |
| HSA | −112.16 | 33.568 | 149.022 | 55.48 | 37.166 | 165.634 | −53.297 | 9.38 | 88.164 | 6.538 | 72.023 | 40.361 | 19.178 | 98.857 |
| PhosB | −113.09 | 12.927 | 24.443 | 9.822 | 15.236 | −7.537 | −56.939 | 1.215 | 18.544 | −0.937 | 22.12 | −15.60 | −0.098 | 48.73 |
| PhosB | −92.767 | 17.571 | 38.022 | 6.761 | 12.95 | 2.046 | −68.368 | −3.456 | 18.961 | −11.20 | 56.033 | −29.84 | 4.388 | 12.773 |
| PhosB | −103.57 | −47.53 | 38.016 | 11.859 | 13.662 | −9.507 | −51.251 | −4.319 | 19.729 | −31.62 | 30.903 | −20.97 | 2.716 | 78.642 |
| PhosB | −104.30 | −19.87 | 181.245 | 14.108 | 7.703 | −54 | −54.676 | −4.998 | 15.061 | −12.90 | 17.532 | −40.43 | −0.935 | 42.59 |
| PhosB | −108.78 | 1.589 | 37.766 | 12.438 | 12.552 | −1.451 | −44.655 | 0.828 | 15.309 | 0.622 | 26.179 | −25.79 | −1.361 | 17.954 |
| PhosB | −102.26 | 10.586 | 30.103 | 8.558 | 14.93 | 26.006 | −38.881 | −32.74 | 23.4 | −28.78 | 30.138 | −21.99 | 6.263 | 61.075 |
| Myo | −56.612 | −72.90 | −49.006 | −4.948 | 3.852 | −124.66 | −72.787 | −4.933 | −7.817 | −2.195 | 4.983 | −12.35 | −9.577 | −122.86 |
| Myo | −54.612 | −83.54 | −57.099 | −6.567 | 4.047 | −104.34 | −71.575 | −6.492 | −11.671 | −27.11 | 5.039 | −25.49 | −12.32 | −148.59 |
| Myo | −60.429 | −82.78 | −49.916 | −3.433 | 7.069 | −117.6 | −75.871 | −5.869 | −8.249 | 1.222 | 4.014 | −22.66 | −11.88 | −132.84 |
| Myo | −66.112 | −73.70 | −44.93 | −7.16 | 3.277 | −82.888 | −73.015 | −4.639 | −11.177 | −10.53 | 3.179 | −25.64 | −12.83 | −139.70 |
| Myo | −58.6 | −79.23 | −41.785 | −4.772 | 2.779 | −124.12 | −73.489 | −18.46 | −11.913 | −5.669 | 5.727 | −22.89 | −11.27 | −123.58 |
| Myo | −57.784 | −63.44 | −49.298 | −11.29 | 6.563 | −114.87 | −75.125 | −2.676 | −9.204 | −14.94 | 9.133 | −19.04 | −7.7 | −141.74 |

TABLE 6

Best combination of GFP-nanoparticle combination for the detection of 11 set of proteins at $A_{280} = 0.005$.
The maximum classification accuracy was obtained 100% using three GFP-nanoparticle combinations. (See, FIG. 9.)

| Protein | NP7 (%) | NP9 (%) | NP12 (%) | All (%) |
|---|---|---|---|---|
| α-Am | 83 | 50 | 17 | 100 |
| BSA | 67 | 33 | 50 | 100 |
| HSA. | 0 | 100 | 100 | 100 |
| Hem | 67 | 100 | 100 | 100 |
| His | 100 | 100 | 100 | 100 |
| Lip | 100 | 50 | 67 | 100 |
| Myo | 100 | 100 | 83 | 100 |
| PhosA | 100 | 83 | 50 | 100 |
| PhosB | 17 | 67 | 83 | 100 |
| SubA | 100 | 100 | 100 | 100 |
| β-Gal | 83 | 100 | 83 | 100 |
| Total | 74 | 80 | 76 | 100 |

TABLE 7

Best combination of GFP-nanoparticle combination for the detection of 11 set of proteins at $A_{280} = 0.0005$.
The maximum classification accuracy was obtained 98% using six GFP-nanoparticle combinations. (See, FIG. 10.)

| Protein | NP1 (%) | NP2 (%) | NP4 (%) | NP7 (%) | NP12 (%) | NP14 (%) | All (%) |
|---|---|---|---|---|---|---|---|
| α-Am | 83 | 67 | 17 | 0 | 67 | 33 | 100 |
| BSA | 33 | 67 | 83 | 33 | 0 | 67 | 100 |
| HSA. | 67 | 17 | 83 | 50 | 100 | 50 | 100 |
| Hem | 0 | 100 | 50 | 50 | 33 | 50 | 100 |
| His | 100 | 100 | 83 | 100 | 100 | 100 | 100 |
| Lip | 83 | 67 | 83 | 33 | 67 | 67 | 100 |
| Myo | 83 | 83 | 83 | 100 | 83 | 100 | 100 |
| PhosA | 67 | 67 | 33 | 67 | 0 | 50 | 100 |
| PhosB | 83 | 17 | 17 | 17 | 0 | 33 | 100 |
| SubA | 50 | 0 | 33 | 50 | 67 | 67 | 83 |
| β-Gal | 50 | 17 | 17 | 83 | 100 | 0 | 100 |
| Total | 64 | 55 | 53 | 53 | 56 | 56 | 98 |

Example 11

Detection of unknown proteins. In the detection of the unknown proteins 48 unknown protein solutions were randomly selected from 11 proteins. According to the protocol we first measure the UV absorption value for each unknown protein solution at 280 nm. According to the Beer-Lambert law the solution was diluted to $A_{280}=0.105$ and $A_{280}=0.0105$ to get the final absorption of 0.005 and 0.0005 respectively in microplate well. The fluorescence response pattern was recorded and assigned on the basis of the training matrix of protein solutions with corresponding absorption value according to the Mahalanobis distance. (See, FIG. 12.)

TABLE 8

Detection and identification of unknown proteins at $A_{280} = 0.005$ using LDA.

| Entry | NP7 | NP9 | NP12 | Identification | Verification |
|---|---|---|---|---|---|
| 1 | 544.858 | 801.234 | 276.301 | Lip | Lip |
| 2 | 449.2588 | 764.0592 | 291.9075 | PhosB | PhosB |
| 3 | −52.1402 | 186.93 | 163.582 | Hem | Hem |
| 4 | 28.65717 | 522.4622 | 130.4385 | β-Gal | β-Gal |
| 5 | 150.445 | 356.919 | 96.54883 | PhosA | PhosA |
| 6 | 589.3213 | 161.9063 | 217.7883 | BSA | BSA |
| 7 | −41.1953 | 316.076 | 8.735 | α-Am | α-Am |
| 8 | 543.3802 | 669.178 | 261.0163 | Lip | Lip |
| 9 | −126.186 | −4.19533 | −32.4983 | SubA | SubA |
| 10 | 6.775333 | 20.402 | 17.78467 | His | His |
| 11 | 150.4867 | 339.1293 | 111.032 | PhosA | PhosA |
| 12 | −80.8103 | −3.21367 | 22.93267 | Myo | Myo |
| 13 | 43.418 | 419.588 | 145.6947 | β-Gal | β-Gal |
| 14 | 11.05567 | 24.06767 | 25.411 | His | His |
| 15 | 516.7483 | 539.42 | 260.4167 | Lip | Lip |
| 16 | −143.637 | 12.83 | −12.3983 | SubA | SubA |
| 17 | 141.669 | 420.7303 | 163.1263 | PhosA | PhosA |
| 18 | −143.407 | −120.493 | −27.321 | SubA | SubA |
| 19 | 280.6173 | 407.8447 | 467.6083 | HAS | HSA |
| 20 | −35.321 | 194.656 | 48.27633 | α-Am | α-Am |
| 21 | 466.3307 | 156.8423 | 278.8327 | BSA | BSA |
| 22 | −142.673 | −119.676 | −5.847 | SubA | SubA |
| 23 | 151.6067 | 296.736 | 94.909 | PhosA | PhosA |
| 24 | −93.4733 | −8.70767 | 60.76333 | Myo | Myo |
| 25 | −43.1667 | −31.7527 | 320.9453 | Hem | Hem |
| 26 | 581.572 | 148.2387 | 217.226 | BSA | BSA |
| 27 | 156.3657 | 364.065 | 247.9657 | β-Gal | β-Gal |
| 28 | −167.211 | −57.4501 | −60.5145 | SubA | SubA |
| 29 | 319.4817 | 518.8733 | 475.0967 | HSA | HSA |
| 30 | −19.308 | −175.402 | 126.2663 | Myo | Myo |
| 31 | 12.63767 | −32.4227 | 310.3073 | Hem | Hem |
| 32 | 364.474 | 711.72 | 330.5717 | PhosB | PhosB |
| 33 | −53.5873 | 106.4657 | 8.881333 | Myo | Myo |
| 34 | −189.206 | −52.146 | −69.3343 | SubA | SubA |
| 35 | 108.8427 | 449.7383 | 109.6813 | PhosA | PhosA |
| 36 | 162.9617 | 681.1903 | 484.961 | HSA | HSA |
| 37 | 558.7443 | 148.9763 | 288.6097 | BSA | BSA |
| 38 | 5.4393 | 30.23333 | 19.40467 | His | His |
| 39 | 354.1517 | 694.6527 | 375.92 | PhosB | PhosB |
| 40 | −34.801 | 124.081 | 44.64233 | α-Am | α-Am |
| 41 | −122.541 | −7.245 | 47.466 | Myo | Myo |
| 42 | 364.2533 | 673.055 | 486.9857 | HSA | HSA |
| 43 | 358.3903 | 651.9387 | 471.9393 | HSA | HSA |
| 44 | −38.9003 | 134.8933 | 232.251 | Hem | Hem |
| 45 | 148.688 | 670.7593 | 177.5123 | β-Gal | β-Gal |
| 46 | 615.7727 | 917.1587 | 279.6903 | Lip | Lip |
| 47 | −64.127 | 1.405333 | 47.78433 | Myo | Myo |
| 48 | 72.33267 | 333.859 | 299.5967 | β-Gal | β-Gal |

TABLE 9

Detection and identification of unknown proteins at $A_{280} = 0.0005$ using LDA.

| Entry | NP1 | NP2 | NP4 | NP7 | NP12 | NP14 | Identification | Verification |
|---|---|---|---|---|---|---|---|---|
| 1 | −74.603 | 14.1485 | 15.2133 | −41.0778 | 17.3395 | 79.40217 | BSA | BSA |
| 2 | −87.609 | 44.8783 | 48.7241 | −34.6437 | 12.098 | 52.577 | Lip | Lip |
| 3 | −75.398 | −47.903 | −19.989 | −63.3603 | 10.711 | −64.8655 | Myo | Myo |
| 4 | −82.103 | −26.070 | 3.7875 | −64.7903 | −14.227 | 29.23267 | PhosB | PhosB |

TABLE 9-continued

Detection and identification of unknown proteins at $A_{280} = 0.0005$ using LDA.

| | Fluorescence response pattern | | | | | | Identi- | Verifi- |
|---|---|---|---|---|---|---|---|---|
| Entry | NP1 | NP2 | NP4 | NP7 | NP12 | NP14 | fication | cation |
| 5 | −118.49 | 1.95366 | 7.85833 | −90.767 | −24.9423 | −41.8097 | PhosB | β-Gal |
| 6 | −162.18 | 38.2683 | 49.8466 | −51.1147 | 38.26 | 103.3648 | HSA | HSA |
| 7 | −88.530 | −26.556 | −8.3231 | −60.9667 | −30.3662 | −31.4635 | SubA | SubA |
| 8 | −95.26 | 104.796 | 45.8066 | 7.100167 | 4.020667 | 198.364 | Lip | Lip |
| 9 | −74.701 | −31.328 | −3.0806 | −91.823 | −79.394 | −52.745 | Hem | Hem |
| 10 | −17.380 | −115.29 | −23.559 | −19.8119 | −48.9773 | −46.9827 | α-Am | α-Am |
| 11 | −35.471 | 39.9196 | 24.745 | −65.5743 | 29.89333 | 50.69367 | PhoA | PhosA |
| 12 | −91.745 | −78.871 | −15.042 | −115.713 | 5.296667 | 32.931 | β-Gal | β-Gal |
| 13 | −104.81 | −9.1351 | 20.4406 | −47.8413 | −25.3407 | −83.0237 | PhosB | PhosB |
| 14 | −19.658 | −24.332 | 4.21833 | −22.71 | −2.3 | −36.8387 | His | His |
| 15 | −164.13 | 39.435 | 27.9783 | 85.475 | 12.57967 | −14.4523 | HSA | HSA |
| 16 | −53.668 | −80.924 | −6.5476 | −84.5993 | −21.4603 | −128.324 | Myo | Myo |
| 17 | −49.099 | −13.330 | 3.27833 | −45.6117 | −28.388 | −111.901 | β-Am | β-Am |
| 18 | −83.100 | −42.600 | −17.146 | −110.521 | −10.351 | −89.2093 | Hem | Hem |
| 19 | −69.056 | 17.6156 | 15.6396 | −41.8793 | 20.926 | 119.5423 | BSA | BSA |
| 20 | −39.47 | 23.4673 | 4.85066 | −15.642 | −7.03733 | −6.805 | PhosA | PhosA |
| 21 | −16.493 | −27.587 | 2.8534 | −29.083 | −4.764 | −38.867 | His | His |
| 22 | −109.11 | −65.788 | −26.363 | −100.691 | −19.056 | 7.182667 | β-Gal | β-Gal |
| 23 | −146.16 | 48.2643 | 38.9823 | −36.9033 | 48.144 | 85.32933 | HSA | HSA |
| 24 | −91.893 | 70.366 | 41.441 | −34.3133 | −17.3277 | 93.269 | Lip | Lip |
| 25 | −79.473 | −67.978 | −11.465 | −107.643 | −12.3223 | −111.874 | SubA | Hem |
| 26 | −47.650 | −15.914 | 4.95166 | −43.717 | −19.9107 | −97.1147 | α-Am | α-Am |
| 27 | −61.342 | −72.338 | −7.92 | −78.8813 | −34.5377 | −127.652 | Myo | Myo |
| 28 | −65.839 | 24.8157 | 15.8093 | −38.251 | 6.785667 | 102.4397 | BSA | BSA |
| 29 | −46.708 | 41.9443 | 8.42233 | −7.18433 | −7.73467 | −4.617 | PhosA | PhosA |
| 30 | −77.443 | −64.481 | −21.777 | −109.628 | −2.51567 | −110.549 | SubA | SubA |
| 31 | −18.624 | −42.431 | 6.69366 | −23.7353 | −4.143 | −42.665 | His | His |
| 32 | −124.68 | −4.0593 | 12.9115 | −35.8473 | −34.0777 | 44.76633 | PhosB | PhosB |
| 33 | −112.70 | −50.566 | −10.932 | −117.319 | 3.7171 | 30.65267 | β-Gal | β-Gal |
| 34 | −91.58 | 14.7186 | 21.864 | −52.4703 | 24.576 | 101.8117 | Lip | Lip |
| 35 | −42.146 | −10.633 | 3.70566 | −42.031 | −25.3643 | −116.787 | α-Am | α-Am |
| 36 | −62.856 | 12.5697 | 16.1422 | −56.148 | 18.56533 | 123.6273 | BSA | BSA |
| 37 | −42.225 | 51.8363 | 17.2913 | −10.3107 | −4.88567 | −11.7223 | PhosA | PhosA |
| 38 | −70.959 | −59.346 | −20.022 | −105.289 | −6.31933 | −100.943 | SubA | SubA |
| 39 | −86.187 | −47.347 | −10.033 | −105.02 | −21.0007 | −89.506 | Hem | Hem |
| 40 | −16.601 | −19.347 | 2.9368 | −26.7927 | −8.15767 | −32.5723 | His | His |
| 41 | −124.97 | 49.219 | 45.8856 | −63.6913 | 59.09 | 84.92 | HSA | HSA |
| 42 | −106.81 | −4.6668 | 13.4866 | −60.869 | −20.1533 | 46.668 | PhosB | PhosB |
| 43 | −47.813 | −73.729 | −7.8303 | −73.7287 | −17.497 | −147.202 | Myo | Myo |
| 44 | −34.704 | −90.950 | 31.4956 | −187.7 | −39.0293 | −197.19 | Lip | SubA |
| 45 | −146.38 | −53.491 | 47.8856 | −24.99 | −35.1117 | −42.2167 | HSA | HSA |
| 46 | −49.886 | −11.092 | 3.801 | −42.8043 | −16.506 | −93.2337 | α-Am | α-Am |
| 47 | −102.56 | −79.654 | −17.242 | −124.84 | −24.8553 | −103.943 | βGal | β-Gal |
| 48 | −50.179 | 49.422 | −33.923 | −119.231 | −4.66533 | −216.692 | Myo | Myo |

While the principles of this invention have been described in connection with specific embodiments, it should be understood clearly that these descriptions are added only by way of example and are not intended to limit, in any way, the scope of this invention. For instance, the present invention can be applied more specifically to the identification of one or more proteins present in a biological fluid such as but not limited to blood, urine, saliva and the like. Likewise, the present invention can be used in conjunction with fluorescence patterns from at least one reference protein mixture, in such a biological fluid, indicative of the health state of a subject. By comparison, as described above, comparison of such a reference pattern with the fluorescence pattern provided by an unknown or test biological fluid can be used to detect the presence of a new, additional or differently expressed protein analyte (e.g., protein biomarker) indicative of a change in health or possible disease state.

We claim:

1. A method of detecting the presence of a protein analyte, the method comprising:
   providing a plurality of non-covalent complexes between a plurality of nanoparticles and a fluorescent polymer,
      wherein each of the plurality of nanoparticles comprises an inner metallic core and a coating layer comprising a cationic ligand,
      wherein the fluorescent polymer comprises an anionic group, and
      wherein fluorescence of the polymer in the non-covalent complexes is quenched;
   mixing a sample to be tested for the presence of the protein analyte with the plurality of the non-covalent complexes under a condition such that, if the protein analyte is present in the sample, at least some of the fluorescent polymer is displaced by the protein analyte, thereby resulting in restoration of at least some of fluorescence of the fluorescent polymer; and measuring a fluorescence pattern of the resulting sample to determine the presence of the protein analyte.

2. The method of claim 1, wherein the plurality of the non-covalent complexes comprise at least three non-covalent complexes between at least three different nanoparticles and a fluorescent polymer.

3. The method of claim 2, wherein the cationic ligand comprises a quaternary ammonium ion.

4. The method of claim 1, wherein the fluorescent polymer is a synthetic π-conjugated polymer.

5. The method of claim 4, wherein the synthetic π-conjugated polymer comprises a structural unit of:

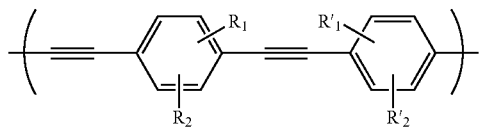

wherein $R_1$ and $R_2$ are independently selected from H, alkyl and oxa-substituted alkyl groups; $R'_1$, and $R'_2$ are independently selected from H and alkyl groups; provided that at least one of $R'_1$, and $R'_2$ comprises a charged group.

6. The method of claim 5, wherein at least one of $R'_1$, and $R'_2$ comprises a carboxylate or a sulfate anion and a counter cation.

7. The method of claim 6, wherein each of $R'_1$, and $R'_2$ is:

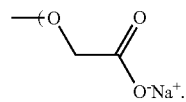

8. The method of claim 5, wherein at least one of $R_1$, and $R_2$ comprises a poly(alkylene oxide) group.

9. The method of claim 5, wherein the coating layer of each of the nanoparticles has covalently bond thereon a cationic ligand having the structure of

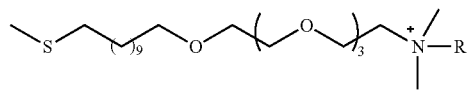

wherein R is selected from:

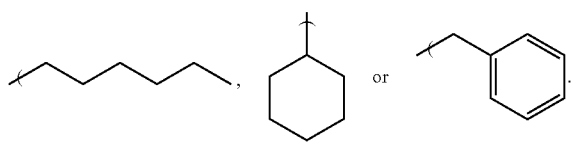

10. The method of claim 1, wherein the sample comprises a plurality of proteins from a lysed cell.

11. The method of claim 1, wherein measuring a fluorescence pattern of the resulting sample to determine the presence of the protein analyte comprises analyzing the fluorescence pattern; and wherein the sample comprises a lysed cell.

12. A method of detecting the presence of a protein analyte, the method comprising:

providing a plurality of non-covalent complexes between a nanoparticle and a plurality of fluorescent polymers, wherein the nanoparticle comprises an inner metallic core and a coating layer comprising a cationic ligand, wherein each of the fluorescent polymers comprises an anionic group, and wherein fluorescence of the fluorescent polymers in the non-covalent complexes is quenched;

mixing a sample to be tested for the presence of the protein analyte with the plurality of the non-covalent complexes under a condition such that, if the protein analyte is present in the sample, at least some of the fluorescent polymers are displaced by the protein analyte, thereby resulting in restoration of at least some of fluorescence of the fluorescent polymers; and measuring a fluorescence pattern of the resulting sample to determine the presence of the protein analyte.

13. The method of claim 12 wherein, the plurality of the non-covalent complexes comprise at least three non-covalent complexes between a nanoparticle and at least three different fluorescent polymers.

14. The method of claim 13 wherein the coating layer of the nanoparticle has covalently bond thereon a cationic ligand having the structure of

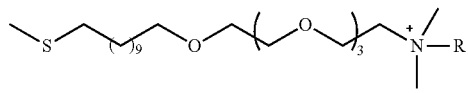

wherein R is selected from:

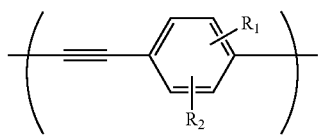

15. The method of claim 12, wherein at least one of the fluorescent polymers is a synthetic π-conjugated polymer.

16. The method of claim 15, wherein each of the π-conjugated polymers comprises a structural unit of:

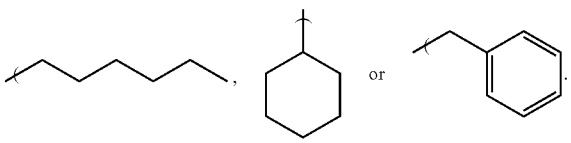

wherein $R_1$ and $R_2$ are independently selected from H, alkyl and oxa-substituted alkyl groups; provided that at least one of $R_1$ and $R_2$ comprises a charged group.

17. The method of claim 16, wherein at least one of $R_1$, and $R_2$ comprises a carboxylate or a sulfate anion and a counter cation.

18. The method of claim 17, wherein the sample comprises a plurality of proteins.

19. The method of claim 12, wherein at least one of the fluorescent polymers is a fluorescent protein.

20. The method of claim 19, wherein the fluorescent polymer comprises a green fluorescent protein.

21. The method of claim 12, wherein measuring a fluorescence pattern of the resulting sample comprises measuring a fluorescent pattern for each of the fluorescent polymers at the same wavelength.

* * * * *